(12) United States Patent
Rommens

(10) Patent No.: US 7,855,319 B2
(45) Date of Patent: Dec. 21, 2010

(54) HIGH LEVEL ANTIOXIDANT-CONTAINING FOODS

(75) Inventor: Caius Rommens, Boise, ID (US)

(73) Assignee: J.R. Simplot Company, Boise, ID (US)

( * ) Notice: Subject to any disclaimer, the term of this patent is extended or adjusted under 35 U.S.C. 154(b) by 571 days.

(21) Appl. No.: 11/822,416

(22) Filed: Jul. 5, 2007

(65) Prior Publication Data

US 2008/0134356 A1    Jun. 5, 2008

Related U.S. Application Data

(60) Provisional application No. 60/818,516, filed on Jul. 6, 2006.

(51) Int. Cl.
*C12N 15/82*     (2006.01)
*C12N 5/14*      (2006.01)
*A01H 5/00*      (2006.01)

(52) U.S. Cl. .................. 800/278; 800/298; 800/317; 800/317.1; 800/317.2; 800/317.3; 800/317.4; 435/410

(58) Field of Classification Search ................. None
See application file for complete search history.

(56) References Cited

U.S. PATENT DOCUMENTS

| | | | |
|---|---|---|---|
| 2003/0221213 | A1 | 11/2003 | Rommens et al. |
| 2004/0003434 | A1 | 1/2004 | Weeks et al. |
| 2004/0107455 | A1 | 6/2004 | Rommens et al. |
| 2005/0034188 | A1 | 2/2005 | Weeks et al. |

FOREIGN PATENT DOCUMENTS

| | | |
|---|---|---|
| EP | 0 154 204 B1 | 1/1994 |
| WO | WO 03/069980 A2 | 8/2003 |
| WO | WO 2005/004585 A2 | 1/2005 |

OTHER PUBLICATIONS

Kang et al, Agricultural Chemistry and Biotechnology, Sep. 2006, vol. 49, No. 3, pp. 75-81.*
Clarisa Start Column, The St Louis Post-Dispatch, Jan. 7, 1989.*
Baumann et al., "The DNA Binding Site of the Dof Protein NtBBF1 is Essential for Tissue-Specific and Auxin-Regulated Expression of the *rolB* Oncogene in Plants", *The Plant Cell*, Mar. 1999, vol. 11, pp. 323-333.
Benzie et al., "The Ferric Reducing Ability of Plasma (FRAP) as a Measure of "Antioxidant Power": The FRAP Assay", *Analytical Biochemistry*, 1996, vol. 239, pp. 70-76.
Bürkle et al., "Transport of Cytokinins Mediated by Purine Transporters of the PUP Family Expressed in Phloem, Hydathodes and Pollen of *Arabidopsis*", 2003, vol. 34, pp. 13-26.
Cao et al., "Oxygen-Radical Absorbance Capacity Assay for Antioxidants", *Free Radical Biology & Medicine*, 1993, vol. 14, pp. 303-311.
Crowley, R. "Determining ORAC", printed from the internet www.convance.com/analytical/news_orac.php, Reprinted from the Dec. 2004 Food Product Design Catalog Showcase.
Glazer, Alexander, "Phycoerythrin Fluorescence-Based Assay for Reactive Oxygen Species", *Methods in Enzymology*, 1990, vol. 186, pp. 161-168.
Held, P., "Performing Oxygen Radical Absorbance Capacity Assays with Synergy™ HT, ORAC Antioxidant Tests, BioTek Application Notes", printed from the internet www.biotek.com/products/tech_res_detail.pho?id=161.
Hellens et al., "pGreen: a Versatile and Flexible Binary Ti Vector for *Agrobacterium*-Mediated Plant Transformation", *Plant Molecular Biology*, 2000, vol. 42, pp. 819-832.
Hinchee et al., "Production of Transgenic Soybean Plants Using *Agrobacterium*-mediated DNA Transfer", *Bio/Technology, Nature Publishing Company*, Aug. 1988, vol. 6, pp. 915-922.
Horsch et al., "A Simple and General Method for Transferring Genes into Plants", *Biological Sciences, Monsanto Company* Mar. 8, 1985, pp. 1229-1231, St. Louis, MO.
Liang et al., "Developmental and environmental regulation of a phenylalanine ammonia-lyase-β-glucuronidase gene fusion in transgenic tobacco plants", *Proc. Natl. Acad. Sci, USA*, Dec. 1989, vol. 86, pp. 9284-9288.
Mattila et al., "Basic Composition and Amino Acid Contents of Mushrooms Cultivated in Finland", *J. Agric. Food Chem.*, 2002, vol. 50, pp. 6419-6422.
Mattila et al., "Determination of Free and Total Phenolic Acids in Plant-Derived Foods by HPLC with Diode-Array Detection", *J. Agric. Food Chem.*, 2002, vol. 50, pp. 3660-3667.
Miki et al., "Procedures for Introducing Foreign DNA into Plants", *Methods in Plant Molecular Biology and Biotechnology*, by CRC Press, Inc., 1993, pp. 67-88.
Niggeweg et al., "Engineering Plants with Increased Levels of the Antioxidant Chlorogenic Acid", *Nature Biotechnology*, Jun. 2004, vol. 22, No. 6.
Potrykus et al., "Direct gene transfer to cells of a graminaceous monocot", *Molecular & General Genetics*, an International Journal 985, 1985, vol. 199, No. 2, pp. 183-188.
Rice-Evans et al., "Total Antioxidant Status in Plasma and Body Fluids", *Methods in Enzymology*, 1994, vol. 234, pp. 279-293.
Rommens et al., "A Transposon Tagging Strategy with Ac on Plant Cell Level in Heterologous Plant Species", *Plant Sciences*, 1991, vol. 74, pp. 99-106.
Rommens, et al., "Plant-Derived Transfer DNAs", *Plant Physiology*, Nov. 2005, vol. 139, pp. 1338-1349.
Shahrzad et al., "Determination of Some Pharmacologically Active Phenolic Acids in Juices by High-Performance Liquid Chromatography", *Journal of Chromatography A*, 1996, vol. 741, pp. 223-231.
Shi et al., "Gibberellin and abscisic acid regulate *GAST1* expression at the level of transcription", *Plant Molecular Biology*, 1998, vol. 38, pp. 1053-1060.
Wayner et al., "Quantitative Measurement of the Total, Peroxyl Radical-trapping Antioxidant Capability of Human Blood Plasma by Controlled Peroxidation", *FEBS 2700*, Jul. 1985, vol. 187, No. 1.

(Continued)

*Primary Examiner*—Eileen B O Hara
(74) *Attorney, Agent, or Firm*—Foley & Lardner LLP

(57) ABSTRACT

The present invention relates to increasing at least one antioxidant level in a plant or plant product by expressing a polynucleotide that encodes a transcription factor, which is active in a flavonoid pathway. Overexpression of, for instance, a novel and newly-identified gene, the mCai gene, in a plant, results in increased accumulation of chlorogenic acid and other related phenolics, which, in turn, increases the levels of beneficial antioxidant in the plant.

28 Claims, 6 Drawing Sheets

OTHER PUBLICATIONS

Wen et al., "A Universal HPLC Method for the Determination of Phenolic Acids in Compound Herbal Medicines", *J. Agric. Food Chem.*, 2005, vol. 53, pp. 6624-6629.

Yan et al., "New Construct Approaches for Efficient Gene Silencing in Plants", Aug. 2006, pp. 1508-1518, vol. 141, Plant Physiology.

Visser, et al., "Expression of a Chimaeric Granule-Bound Starch Synthase-GUS Gene in Transgenic Potato Plants", 1991, pp. 691-699, vol. 17, *Plant Molecular Biology*, Belgium.

Guevara-Garcia, et al., "A 42 bp Fragment of the *pmas1'* Promoter Containing an *ocs*-Like Element Confers a Developmental, Wound- and Chemically Inducible Expression Pattern", 1998, pp. 743-753, vol. 38, *Plant Molecular Biology*, The Netherlands.

Jung et al., "The Potato *P* Lucus Codes for Flavonoid 3',5'-Hydroxylase", 2005, pp. 269-275, vol. 110, *Theor. Appl. Genet.*, USA.

Bushman et al., "Two Loci Exert Major Effects on Chlorogenic Acid Synthesis in Maize Silks", *Crop Science*, Sep.-Oct. 2002, pp. 1669-1678, vol. 42.

Dixon, Richard A., "A Two-for-One in Tomato Nutritional Enhancement", *Nature Biotechnology*, Jul. 2005, pp. 825-826, vol. 23, No. 7, Nature Publishing Group.

Mathews, et al., "Activation Tagging in Tomato Identifies a Transcriptional Regulator of Anthocyanin Biosynthesis, Modification, and Transport", *The Plant Cell*, Aug. 2003, pp. 1689-1730, vol. 15, American Society of Plant Biologists.

\* cited by examiner

Figure 1.

```
StCAI      --MNSTSMSSLG-VRKGSWTDEEDFLLRKCIDKYGEGKWHLVPARAGLNRCRKSCRLRWL  57
LeANT1     --MNSTSMSSLG-VRKGSWTDEEDFLLRKCIDKYGEGKWHLVPIRAGLNRCRKSCRLRWL  57
StAN2      ---------------KGSWTEQEDFLLRKCIQIYGEGKWHLVPARAGLNRCRKSCRLRWL  45
StANT1     ---TPMMCTSLGVIRKGSWTEEEDILLRKCIDKYGEGKWNLVPTRAGLNRCRKSCRLRWL  57
CaA        --MNTAIIAKSSGVRKGAWTEEEDFLLRKCIQNYGEGKWHLVPIRAGLNRCRKSCRLRWL  58
PhAN2      ---MSTSNASTSGVRKGAWTEEEDLLLRECIDKYGEGKWHLVPVRAGLNRCRKSCRLRWL  57
V1MYBA1    ---MESLG-----VRKGAWIQEEDVLLRKCIEKYGEGKWHLVPLRAGLNRCRKSCRLRWL  52
IpMYB1     --MVNSSARWSPRVRKGAWSEEEDDLLRKCIQKFGEGKWHLVPFRAGLNRCRKSCRLRWL  58
AmVENOSA   -MGNNPLG-----VRKGTWTKEEDILLKQCIEKYGEGKWHQVPIRAGLNRCRKSCRMRWL  54
AtPAP1     ------MEGSSKGLRKGAWTTEEDSLLRQCINKYGEGKWHQVPVRAGLNRCRKSCRLRWL  54
ZmC1       MGRRA--CCAKEGVKRGAWTAKEDDTLAAYVKAHGEGKWREVPQKAGLRRCGKSCRLRWL  58
AtTT2      MGKRATTSVRREELNRGAWTDHEDKILRDYITTHGEGKWSTLPNQAGLKRCGKSCRLRWK  60
              :*:*   .**    *    .*****  :*  .*** ** ****:**

StCAI      NYLRPHIKRGDFAPDEVDLILRLHKLLGNRWSLIAGRLPGRTANDVKNYWNTNLLRSKVN  117
LeANT1     NYLRPHIKRGDFEQDEVDLILRLHKLLGNRWSLIAGRLPGRTANDVKNYWNTNLLR-KLN  116
StAN2      NYLRPHIKRGDFAPDEVDLILRLHKLLGNRWSLIAGRLPGRTANDVKNYWNTHFQK-KLN  104
StANT1     NYLRPHIKRGDFDWDEVDLILRLHKLLGNRWSLIAGRLPGRTANDVKNYWNTNLLR-KLN  116
CaA        NYLRPHIKRGDFGWDEIDLILRLHKLLGNRWSLIAGRLPGRTANDVKNYWNSHLQK---K  115
PhAN2      NYLRPHIKRGDFSLDEVDLILRLHKLLGNRWSLIAGRLPGRTANDVKNYWNTHLRK---K  114
V1MYBA1    NYLKPDIKRGEFALDEVDLMIRLHNLLGNRWSLIAGRLPGRTANDVKNYWHGHHLKKKVQ  112
IpMYB1     NYLHPDIKRGHFSLEEADLILRLHKLLGNRWSLIAGRIPGRTANDVKNYWHSHLKKKVVS  118
AmVENOSA   NYLSPNIKRGSFTRDEVDLIVRLHKLLGNRWSLIAGRLPGRTGNDVKNFWNTHFEKKSGE  114
AtPAP1     NYLKPSIKRGKLSSDEVDLLLRLHKLLGNRWSLIAGRLPGRTANDVKNYWNTHLSKKHEP  114
ZmC1       NYLRPNIKRGNISYDEEDLIVRLHKLLGNRWSLIAGRLPGRTDNEIKNYWNSTLGRRAGA  118
AtTT2      NYLRPGIKRGNISSDEEELIIRLHNLLGNRWSLIAGRLPGRTDNEIKNHWNSNLRKRLPK  120
           *** * ****   :*  :*::***.*************:****  *:;:**.*:

StCAI      ITTKFV-----PHEKINN-----KCGEI---------TKNEIIKPQPRKYFSSTKKN---  155
LeANT1     -TTKIV-----PREKINN-----KCGEIS--------TKIEIIKPQRRKYFSSTMKN---  154
StAN2      IITPPPRPRPNPHLHIKH-----KSIVV---------TKNEIIRPQPR-NFSNVKKNNSH  149
StANT1     TSTKFAP---QPQEGINT-----STIAPQPQEGIKCGKANAIIRPQPQKFRSSMKIN-VS  167
CaA        LITAPHR-----QEKKYN-----TALKI---------TTKNVLRPRPRTFSSSAKNN-IS  155
PhAN2      LIAPHDQ-----KQESKN-----KAVKI---------TENNIIKPRPRTFSRPAMNN--F  153
V1MYBA1    FQEEGRN-----KPLTHS-----KTKA---------------IKPHPKFSKALPRF---  144
IpMYB1     MHMASSN-----SSRQDNNWDDEKGKAPQI-------KENILFRPRPRRFFRTSLSS---  163
AmVENOSA   RENTENI-----NPKLIN------SSN------------IIKPQPRTFLKLRPKE---  146
AtPAP1     CCKIKMK-----KRDITP-----IPTTP--------ALKNNVYKPRPRSFTVNNDCN---  153
ZmC1       AGAS--------RVVFAP-----DTGS-----------------HATPAASGSREMTGG---  147
AtTT2      TQTKQPK-----RIKHST-----NNENNVC----------VIRTKAIRCSKTLLFS---  156

StCAI      -ITNNIVIVD----KEEHCKEIIS---EKQTPD--ALMENVDQWWTNLLENCNDDVEEEE  205
LeANT1     -VTNNNVILD----EEEHCKEIIS---EKQTPD--ASMDNVDPWWINLLENCNDDIEEDE  204
StAN2      WCNNKSMITNTLDKDDKRCKEIVVNISEKPTRENTSSIDDGVQWWTNLLENCN---EIEE  206
StANT1     WCNNNSIVNN---------------EEASKD-----NNDMQWWANILENCNDIGEGEA  205
CaA        WCTNKSTVITNTLDKDERDKEIGLNICQKLTSETSSTIDDGVQWWTSLLENCK---EIEE  212
PhAN2      PCWNGKSCNKNTIDKNEGDTEIIKFSDEKQKPE--ESIDDGLQWWANLLANNIEIEELVS  211
V1MYBA1    --ELKTTAVD-----TFDTQVSTSSKPSSTSPQPNDDIIWWESLLAELDQETD--FSASG  195
IpMYB1     --PALSTLTG-----KAKAVVYDAPPPPPPPHQLQPQPEATSPAADLLMVFN--VQQNS  214
AmVENOSA   --TKKQKNIR-----NVCTANDDKQQPLSTSG-QLEEVNERIRWWSELLDFAD--YVD--  194
AtPAP1     -HLNAPPKVD------VNPPCLGLNINNVCDNSIIYNKDKKKDQLVNNLIDGD-------  199
ZmC1       QKGAAPRADLGSPGSAAVVWAPKAARCTGGLFFHRDTPHAGETETPTPMMMAGGGGGEAR  207
AtTT2      DLSLQKKSSTSPLPLKEQEMDQGGSSLMGDLEFDFDRIHS-EFHFPDLMDFDGLDCG---  212

StCAI      EEAVTNYEKTLTSLLN--------GEGNSMQQGQISHESWGDFSLNLPPMQLGE-NDDF  255
LeANT1     E-VVINYEKTLTSLLHEEISPPLNIGEGNSMQQGQISHENWGEFSLNLPPMQQGVQNDDF  263
StAN2      EVAVTNFEKTPTMLLHEEISPPLINGEGNSMQQGQ-SHD-W---------------DDF  248
StANT1     ERTLPSCKEINCNEIDK--TPSLLHDGGNSTQQG-GDGGW---------------DEF  246
CaA        DVAAVGIFEEKNKLVPS-----LLHDEINSLTMQQGQSDGW---------------DDF  251
PhAN2      CNSPTLLHEETAPSVN---------AESSLTQGGGSGL-----------------SDF  243
V1MYBA1    EMLIASLRAEETATQKKG-----------PMDGMIEQIQGG---------------EGDF  229
IpMYB1     NSIETNLPAQTTAPSSHDGVKWWEDLLYDDSHQGLIDWTT----------------DDDF  258
AmVENOSA   ----------------------------------------------------
AtPAP1     NMWLEKFLEESQ--------------EVDILVPEATTTEKG---------------DTL  229
ZmC1       SSDDCSSAASVSPLVGSSQHDPCFSGDGDGDWMDDVRALAS---------------FLE-  251
AtTT2      ---NVTSLVSSNEILG-----ELVPAQGN---LDLNRPFTS---------------CHHR  246

StCAI      SAEI-DLWNLLD-------  266
LeANT1     SAEI-DLWNLLD-------  274
StAN2      STDI-DLWNLLN-------  259
StANT1     SLD--DIWNLLN-------  256
CaA        SADI-DLWNLLN-------  262
PhAN2      SVDIDDIWDLVS-------  255
V1MYBA1    PFDV-GFWDTPNTQVNHLI  247
IpMYB1     PIDV-TLLKLLDTTI----  272
AmVENOSA   -------------------
AtPAP1     AFDVDQLWSLFDGETVKFD  248
ZmC1       -SDEEWLRCHTAEQLV---  266
AtTT2      GDDEDWLRDFTC-------  258
```

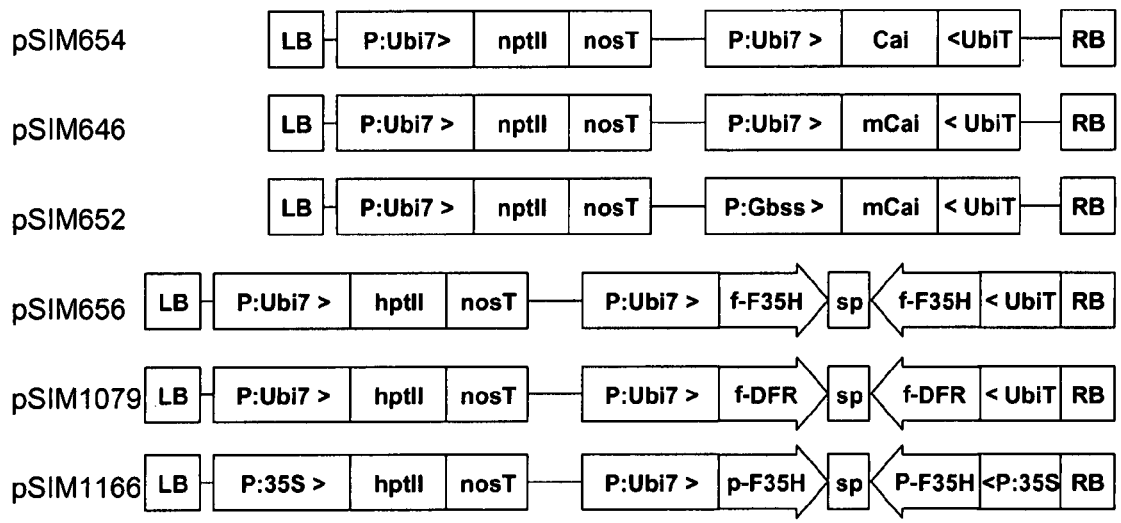
Figure 2. Transfer DNAs of binary vectors

SEQUENCE LISTING

<160> NUMBER OF SEQ ID NOS: 27

<210> SEQ ID NO 1
<211> LENGTH: 968
<212> TYPE: DNA
<213> ORGANISM: Solanum tuberosum

<400> SEQUENCE: 1

```
atgaacagtt cacctatgtc ttcattggga gtgaggaaag gttcatggac tgatgaagaa      60
gattttcttt taagaaaatg tattgataag tatggtgaag gaaaatggca tcttgttcct     120
gctagagctg gtaattaaac taactaccgt gctattttat ctgtctgtct cattttatgt     180
gacattcttt gtaaaatgta tgtacgtgca ggtctgaata gatgtcggaa aagttgtaga     240
ctgaggtggc tgaattatct aaggccacat atcaagagag gtgactttgc tccggatgaa     300
gtggatctca ttttgaggct tcataagctc ttaggcaaca ggcatgctag tttatgtttt     360
gacaaatttg attaatataa tatatatgtg tgactatttc atctaaacgt tacgttatta     420
tatgtagatg gtcacttatt gctggtagac ttccaggaag gacagcaaac gatgtgaaaa     480
actattggaa cacaaacctt ctaaggagta aggtaaatat tactactaaa tttgttcctc     540
atgaaaagat taacaataag tgtggagaaa ttactaagaa tgaaataata aaacctcaac     600
cacgaaagta tttctcaagc acaagaaga atattacaaa caatattgta attgtggaca     660
aggaggaaca ttgcaaggaa ataataagtg agaagcaaac tccagatgca ttgatggaaa     720
acgtagatca atggtggaca aatttactgg aaaattgcaa tgacgatgtt gaagaagaag     780
aagaagaagc tgtaactaat tatgaaaaaa cacttacaag tttgttaaat ggtgaaggta     840
actccatgca acaaggacaa ataagtcatg aaagttgggg tgacttttct cttaatttac     900
cacccatgca actaggagaa aatgatgatt tttctgctga aattgactta tggaatctac     960
``` ttgattaa                                                              968

<210> SEQ ID NO 2
<211> LENGTH: 801
<212> TYPE: DNA
<213> ORGANISM: Solanum tuberosum

<400> SEQUENCE: 2
atgaacagtt cacctatgtc ttcattggga gtgaggaaag gttcatggac tgatgaagaa      60
gattttcttt taagaaaatg tattgataag tacggtgaag gaaagtggca tcttgttcct     120
gctagagctg gtctgaatag atgtcggaaa agttgtagac tgaggtggct gaattatcta     180
aggccacata tcaagagagg tgactttgct ccggatgaag tggatctcat tttgaggctt     240
cataagctct taggcaacag atggtcactt attgctggta acttccagg aaggacagca     300
aacgatgtga aaactattg gaacacaaac cttctaagga gtaaggtaaa tattactact     360
aaatttgttc ctcatgaaaa gattaacaat aagtgtggag aaattactaa gaatgaaata     420
ataaaaccctc aaccacgaaa gtatttctca agcacaaaga gaatattac aaacaatatt     480
gtaattgtgg acaaggagga acattgcaag gaaataataa gtgagaagca actccagat     540
gcattgatgg aaaacgtaga tcaatggtgg acaaatttac tggaaaattg caatgacgat     600
gttgaagaag aagaagaaga agctgtaact aattatgaaa aaacacttac aagtttgtta     660
aatggtgaag gtaactccat gcaacaagga caaataagtc atgaaagttg gggtgacttt     720
tctcttaatt taccacccat gcaactagga gaaaatgatg atttttctgc tgaaattgac     780
ttatggaatc tacttgatta a                                                801

<210> SEQ ID NO 3
<211> LENGTH: 968
<212> TYPE: DNA
<213> ORGANISM: Solanum tuberosum

<400> SEQUENCE: 3
atgaacagta catctatgtc ttcattggga gtgaggaaag gttcatggac tgatgaagaa      60
gattttcttt taagaaaatg tattgataag tatggtgaag gaaaatggca tcttgttcct     120
gctagagctg gtaattaaac taactaccgt gctattttat ctgtctgtct catttatgt     180
gacattcttt gtaaaatgta tgtacgtgca ggtctgaata gatgtcggaa aagttgtaga     240
ctgaggtggc tgaattatct aaggccacat atcaagagag tgactttgct ccggatgaa     300
gtggatctca ttttgaggct tcataagctc ttaggcaaca ggcatgctag tttatgtttt     360
gacaaatttg attaatataa tatatatgtg tgactatttc atctaaacgt tacgttatta     420
tatgtagatg gtcacttatt gctggtagac ttccaggaag gacagcaaac gatgtgaaaa     480
actattggaa cacaaacctt ctaaggagta aggtaaatat tactactaaa tttgttcctc     540
atgaaaagat taacaataag tgtggagaaa ttactaagaa tgaataata aaacctcaac     600
cacgaaagta tttctcaagc acaagaaga atattacaaa caatattgta attgtggaca     660
aggaggaaca ttgcaaggaa ataataagtg agaagcaaac tccagatgca ttgatggaaa     720
acgtagatca atggtggaca aatttactgg aaaattgcaa tgacgatgtt gaagaagaag     780
aagaagaagc tgtaactaat tatgaaaaaa cacttacaag tttgttaaat ggtgaaggta     840
actccatgca acaaggacaa ataagtcatg aaagttgggg tgactttct cttaatttac     900
cacccatgca actaggagaa aatgatgatt tttctgctga aattgactta tggaatctac     960
ttgattaa                                                             968

<210> SEQ ID NO 4
<211> LENGTH: 266
<212> TYPE: PRT
<213> ORGANISM: Solanum tuberosum

<400> SEQUENCE: 4

Met Asn Ser Ser Pro Met Ser Ser Leu Gly Val Arg Lys Gly Ser Trp
1               5                   10                  15

Thr Asp Glu Glu Asp Phe Leu Leu Arg Lys Cys Ile Asp Lys Tyr Gly
            20                  25                  30

Glu Gly Lys Trp His Leu Val Pro Ala Arg Ala Gly Leu Asn Arg Cys
        35                  40                  45

Arg Lys Ser Cys Arg Leu Arg Trp Leu Asn Tyr Leu Arg Pro His Ile
    50                  55                  60

Lys Arg Gly Asp Phe Ala Pro Asp Glu Val Asp Leu Ile Leu Arg Leu
65                  70                  75                  80

His Lys Leu Leu Gly Asn Arg Trp Ser Leu Ile Ala Gly Arg Leu Pro
                85                  90                  95

Gly Arg Thr Ala Asn Asp Val Lys Asn Tyr Trp Asn Thr Asn Leu Leu
            100                 105                 110

Arg Ser Lys Val Asn Ile Thr Thr Lys Phe Val Pro His Glu Lys Ile
        115                 120                 125

Asn Asn Lys Cys Gly Glu Ile Thr Lys Asn Glu Ile Ile Lys Pro Gln
    130                 135                 140

Pro Arg Lys Tyr Phe Ser Ser Thr Lys Asn Ile Thr Asn Asn Ile
145                 150                 155                 160

Val Ile Val Asp Lys Glu His Cys Lys Glu Ile Ser Glu Lys
                165                 170                 175

Gln Thr Pro Asp Ala Leu Met Glu Asn Val Asp Gln Trp Trp Thr Asn
            180                 185                 190

Leu Leu Glu Asn Cys Asn Asp Asp Val Glu Glu Glu Glu Glu Glu Ala
        195                 200                 205

Val Thr Asn Tyr Glu Lys Thr Leu Thr Ser Leu Leu Asn Gly Glu Gly
    210                 215                 220

Asn Ser Met Gln Gln Gly Gln Ile Ser His Glu Ser Trp Gly Asp Phe
225                 230                 235                 240

Ser Leu Asn Leu Pro Pro Met Gln Leu Gly Glu Asn Asp Asp Phe Ser
                245                 250                 255

Ala Glu Ile Asp Leu Trp Asn Leu Leu Asp
            260                 265

<210> SEQ ID NO 5
<211> LENGTH: 266
<212> TYPE: PRT
<213> ORGANISM: Solanum tuberosum

<400> SEQUENCE: 5

Met Asn Ser Thr Ser Met Ser Ser Leu Gly Val Arg Lys Gly Ser Trp
1               5                   10                  15

Thr Asp Glu Glu Asp Phe Leu Leu Arg Lys Cys Ile Asp Lys Tyr Gly
            20                  25                  30

Glu Gly Lys Trp His Leu Val Pro Ala Arg Ala Gly Leu Asn Arg Cys
        35                  40                  45

Arg Lys Ser Cys Arg Leu Arg Trp Leu Asn Tyr Leu Arg Pro His Ile

```
                50                   55                   60
Lys Arg Gly Asp Phe Ala Pro Asp Glu Val Asp Leu Ile Leu Arg Leu
 65                  70                  75                  80

His Lys Leu Leu Gly Asn Arg Trp Ser Leu Ile Ala Gly Arg Leu Pro
                 85                  90                  95

Gly Arg Thr Ala Asn Asp Val Lys Asn Tyr Trp Asn Thr Asn Leu Leu
            100                 105                 110

Arg Ser Lys Val Asn Ile Thr Thr Lys Phe Val Pro His Glu Lys Ile
        115                 120                 125

Asn Asn Lys Cys Gly Glu Ile Thr Lys Asn Glu Ile Ile Lys Pro Gln
    130                 135                 140

Pro Arg Lys Tyr Phe Ser Ser Thr Lys Lys Asn Ile Thr Asn Asn Ile
145                 150                 155                 160

Val Ile Val Asp Lys Glu Glu His Cys Lys Glu Ile Ile Ser Glu Lys
                165                 170                 175

Gln Thr Pro Asp Ala Leu Met Glu Asn Val Asp Gln Trp Trp Thr Asn
            180                 185                 190

Leu Leu Glu Asn Cys Asn Asp Asp Val Glu Glu Glu Glu Glu Glu Ala
        195                 200                 205

Val Thr Asn Tyr Glu Lys Thr Leu Thr Ser Leu Leu Asn Gly Glu Gly
    210                 215                 220

Asn Ser Met Gln Gln Gly Gln Ile Ser His Glu Ser Trp Gly Asp Phe
225                 230                 235                 240

Ser Leu Asn Leu Pro Pro Met Gln Leu Gly Glu Asn Asp Asp Phe Ser
                245                 250                 255

Ala Glu Ile Asp Leu Trp Asn Leu Leu Asp
            260                 265

<210> SEQ ID NO 6
<211> LENGTH: 688
<212> TYPE: DNA
<213> ORGANISM: Solanum tuberosum

<400> SEQUENCE: 6
cgaaccatgc atctcaatct taatactaaa aaatgcaaca aaattctagt ggagggacca      60
gtaccagtac attagatatt atcttttatt actataataa tatttttaatt aacacgagac    120 ataggaatgt caagtggtag cggtaggagg gagttggttc agttttttag atactaggag     180
acagaaccgg aggggcccat tgcaaggccc aagttgaagt ccagccgtga atcaacaaag     240
agagggccca taatactgtc gatgagcatt tccctataat acagtgtcca cagttgcctt     300
ccgctaaggg atagccaccc gctattctct tgacacgtgt cactgaaacc tgctacaaat     360
aaggcaggca cctcctcatt ctcacactca ctcactcaca cagctcaaca agtggtaact     420
tttactcatc tcctccaatt atttctgatt tcatgcatgt ttccctacat tctattatga     480
atcgtgttat ggtgtataaa cgttgtttca tatctcatct catctattct gattttgatt     540
ctcttgccta ctgaatttga ccctactgta atcggtgata aatgtgaatg cttcctcttc     600
ttcttcttct tctcagaaat caatttctgt tttgttttttg ttcatctgta gcttggtaga     660 ttccccttttt tgtagaccac acatcacg                                       688

<210> SEQ ID NO 7
<211> LENGTH: 2262
<212> TYPE: DNA
<213> ORGANISM: Solanum tuberosum
```

<400> SEQUENCE: 7

```
caagtgtctg agacaaccaa aactgaaagt gggaaaccaa actctaagtc aaagacttta      60
tatacaaaat ggtataaata taattattta atttactatc gggttatcga ttaacccgtt     120
aagaaaaaac ttcaaaccgt taagaaccga taacccgata acaaaaaaaa tctaaatcgt     180
tatcaaaacc gctaaactaa taacccaata ttgataaacc ataactttt tttattcggg      240
ttatcggttt cagttctgtt tggaacaatc ctagtgtcct aattattgtt ttgagaacca     300
agaaaacaaa aacttacgtc gcaaatattt cagtaaatac ttgtatatct cagtgataat     360
tgatttccaa catgtataat tatcatttac gtaataatag atggtttccg aaacttacgc     420
ttccctttt tcttttgcag tcgtatggaa taaagttgg atatggaggc attcccgggc       480
cttcaggtgg aagagacgga gctgcttcac aaggaggggg ttgttgtact tgaaaatggg     540
catttattgt tcgcaaacct atcatgttcc tatggttgtt tatttgtagt ttggtgttct     600
taatatcgag tgttctttag tttgttcctt ttaatgaaag gataatatct gtgcaaaaat     660
aagtaaattc ggtacataaa gacattttt tttgcatttt ctgtttatgg agttgtcaaa      720
tgtgaattta tttcatagca tgtgagtttc ctctcctttt tcatgtgccc ttgggccttg     780
catgtttctt gcaccgcagt gtgccagggc tgtcggcaga tggacataaa tggcacaccg     840
ctcggctcgt ggaaagagta tggtcagttt cattgataag tatttactcg tattcggtgt     900
ttacatcaag ttaatatgtt caaacacatg tgatatcata catccattag ttaagtataa     960
atgccaactt tttacttgaa tcgccgaata aatttactta cgtccaatat ttagttttgt    1020
gtgtcaaaca tatcatgcac tatttgatta agaataaata aacgatgtgt aatttgaaaa    1080
ccaattagaa aagaagtatg acgggattga tgttctgtga aatcactggt aaattggacg    1140
gacgatgaaa tttgatcgtc catttaagca tagcaacatg ggtctttagt catcatcatt    1200
atgttataat tattttcttg aaacttgata caccaacttt cattgggaaa gtgacagcat    1260
agtataaact ataatatcaa ttctggcaat ttcgaattat tccaaatctc ttttgtcatt    1320
tcatttcctc ccctatgtct gcaagtacca attatttaag tacaaaaaat cttgattaaa    1380
caatttattt tctcactaat aatcacattt aatcatcaac ggttcataca cgtctgtcac    1440
tcttttttta ttctctcaag cgcatgtgat cataccaatt atttaaatac aaaaaatctt    1500
gattaaacaa ttcagtttct cactaataat cacatttaat catcaacggt tcatacacat    1560
ccgtcactct tttttattc tctcaagcgc atgtgatcat accaattatt taaatacaaa    1620
aaatcttgat taaacaattc attttctcac taataatcac atttaatcat caacggttta    1680
tacacgtccg ccactctttt tttattctct caagcgtatg tgatcatatc taactctcgt    1740
gcaaacaagt gaaatgacgt tcactaataa ataatctttt gaatactttg ttcagtttaa    1800
tttatttaat ttgataagaa ttttttttatt attgaatttt tattgtttta aattaaaaat    1860
aagtaaaata tatcaaaata tcttttaatt ttattttga aaaataacgt agttcaaaca     1920
aattaaaatt gagtaactgt ttttcgaaaa ataatgattc taatagtata ttcttttca    1980
tcattagata ttttttttaa gctaagtaca aaagtcatat ttcaatcccc aaaatagcct    2040
caatcacaag aaatgcttaa atccccaaaa taccctcaat cacaagacgt gtgtaccaat    2100
catacctatg gtcctctcgt aaattccgac aaaatcaggt ctataaagtt acccttgata    2160
tcagtattat aaaactaaaa atctcagctg taattcaagt gcaatcacac tctaccacac    2220
actctctagt agagagatca gttgataaca agcttgttaa cg                       2262
```

<210> SEQ ID NO 8
<211> LENGTH: 2019
<212> TYPE: DNA
<213> ORGANISM: Solanum tuberosum

<400> SEQUENCE: 8

```
gatcctttat caatcagatt tgaacatata aataaatata aattgtctca ataattctac      60
attaaactaa tatttgaaat ctcaatttta tgattttta aattcactt atatccaaga      120
caatttcagc ttaaaaagtt ttattaatat ttacattagt tttgttgatg aggatgacaa      180
gattttggtc atcaattaca tatacccaaa ttgaatagta agcaacttaa tgttttcat      240
aatgataatg acagacacaa aaaaaaccca tttattattc acattgattg agttttatat      300
gcaatatagt aataataata atatttctta taaagcaaga ggtcaatttt ttttaatta      360
taccaacgtc actaaattat atttgataat gtaaacaat tcaattttac ttaaatatca      420
tgaaataaac tattttata accaaattac taaattttc caataaaaaa aagtcattaa      480
gaagacataa aataaatttg agtaaaaaga gtgaagtcga ctgacttttt tttttttat      540
cataagaaaa taattatta actttaacct aataaaacac taatataatt tcatggaatc      600
taatacttac ctcttagaaa taagaaaaag tgtttctaat agaccctcaa tttacattaa      660
atattttcaa tcaatttaa ataacaaata tcaatgagg gtcaataaca atatcaaaat      720
aatatgaaaa aagagcaata cataatataa gaaagaagat ttaagtgcga ttatcaaggt      780
agtattatat cctaatttgc taatatttaa actcttatat ttaaggtcat gttcatgata      840
aacttgaaat gcgctatatt agagcatata ttaaaataaa aaaatacctaa aataaaatt      900
aagttatttt tagtatatat tttttacat gacctacatt tttctgggtt tttctaaagg      960
agcgtgtaag tgtcgacctc attctcctaa ttttccccac cacataaaaa ttaaaaagga     1020
aaggtagctt tgcgtgttg ttttggtaca ctacacctca ttattacacg tgtcctcata     1080
taattggtta accctatgag gcggttcgt ctagagtcgg ccatgccatc tataaaatga     1140
agctttctgc acctcatttt ttcatcttc tatctgattt ctattataat ttctctcaat     1200
tgccttcaaa tttctctta aggttagaaa tcttctctat ttttggtttt tgtctgttta     1260
gattctcgaa ttagctaatc aggtgctgtt atagccctta attttgagtt ttttttcggt     1320
tgtcttgatg gaaaaggcct aaaatttgag ttttttacg ttggtttgat ggaaaaggcc     1380
tacaattgga gttttccccg ttgttttgat gaaaaagccc ctagtttgag atttttttc     1440
tgtcgattcg attctaaagg tttaaaatta gagttttac atttgtttga tgaaaaaggc     1500
cttaaatttg agttttccg gttgatttga tgaaaaagcc ctagaatttg tgtttttcg     1560
tcggtttgat tctgaaggcc taaaatttga gtttctccgg ctgttttgat gaaaaagccc     1620
taaatttgag tttctccggc tgttttgatg aaaaagccct aaatttgagt ttttccccg     1680
tgtttagat tgtttggttt taattctcga atcagctaat cagggagtgt gaaaagccct     1740
aaatttgagt ttttcgtt gttctgattg ttgtttttat gaatttgcag atgcagatct     1800
ttgtgaaaac tctcaccgga aagactatca ccctagaggt ggaaagttct gatacaatcg     1860
acaacgttaa ggctaagatc aggataagg aaggaattcc cccggatcag caaaggctta     1920
tcttcgccgg aaagcagttg gaggacggac gtactctagc tgattacaac atccagaagg     1980
agtctaccct ccatttggtg ctccgtctac gtggaggtg                           2019
```

<210> SEQ ID NO 9
<211> LENGTH: 267
<212> TYPE: DNA

<213> ORGANISM: Solanum tuberosum

<400> SEQUENCE: 9

| | | | | | |
|---|---|---|---|---|---|
| gatccaaaaa | gcacaagaag | aaatggacca | agtaattggc | aaaaatagac | gtttaattga | 60 |
| atctgatatt | ccaaatcttc | cttatttacg | tgcaatttgc | aaagaaacat | ttcggaaaca | 120 |
| tccttcaaca | ccactaaatc | tccctagagt | atcgaccgag | ccgtgcacgg | tcgatggtta | 180 |
| ctacataccg | aaaaatacta | gacttagtgt | caacatatgg | gcaatcggac | gagatcctga | 240 |
| tgtgtgggag | aatccacttg | agttcag | | | | 267 |

<210> SEQ ID NO 10
<211> LENGTH: 789
<212> TYPE: DNA
<213> ORGANISM: Solanum tuberosum

<400> SEQUENCE: 10

| | | | | | |
|---|---|---|---|---|---|
| ggatccaaaa | agcacaagaa | gaaatggacc | aagtaattgg | caaaaataga | cgtttaattg | 60 |
| aatctgatat | tccaaatctt | ccttatttac | gtgcaatttg | caaagaaaca | tttcggaaac | 120 |
| atccttcaac | accactaaat | ctccctagag | tatcgaccga | gccgtgcacg | gtcgatggtt | 180 |
| actacatacc | gaaaaatact | agacttagtg | tcaacatatg | ggcaatcgga | cgagatcctg | 240 |
| atgtgtggga | gaatccactt | gagttcagaa | ttcgtggtaa | cttttactca | tctcctccaa | 300 |
| ttatttctga | tttcatgcat | gtttccctac | attctattat | gaatcgtgtt | atggtgtata | 360 |
| aacgttgttt | catatctcat | ctcatctatt | ctgattttga | ttctcttgcc | tactgaattt | 420 |
| gaccctactg | taatcggtga | taaatgtgaa | tgcttcctct | tcttcttctt | cttctcagaa | 480 |
| atcaatttct | gttttgtttt | tgttcatctg | tagcttgata | tctgaactca | agtggattct | 540 |
| cccacacgtc | aggatctcgt | ccgattgccc | atatgttgac | actgagtcta | gtattttcg | 600 |
| gtatgtagta | accatcgacc | gtgcacggct | cggtcgatac | tctagggaga | tttagtggtg | 660 |
| ttgaaggatg | tttccgaaat | gtttctttgc | aaattgcacg | taaataagga | agatttggaa | 720 |
| tatcagattc | aattaaacgt | ctattttgc | caattacttg | gtccatttct | tcttgtgctt | 780 |
| tttactagt | | | | | | 789 |

<210> SEQ ID NO 11
<211> LENGTH: 1547
<212> TYPE: DNA
<213> ORGANISM: Solanum tuberosum

<400> SEQUENCE: 11

| | | | | | |
|---|---|---|---|---|---|
| tctagaggtt | ggggtaccga | ttatgttcgg | atcagtttac | acatattttg | attaatttta | 60 |
| agaaatactt | gttatttttc | atcaatacaa | atattggata | aattcattca | caaagtaata | 120 |
| ttctccccct | ctattaagta | gtacaatttc | tatttcaatt | tatgtagcga | tgtttgactg | 180 |
| aacacaaagt | ttcagaaaaa | aagaaagaaa | gagacttag | aaatttacga | tcaaaaacaa | 240 |
| acacccacat | ttgtccgggt | aaatataatt | ggatccttac | ataaaaataa | atagctgtca | 300 |
| gattcattat | tattattatt | ttgtcagtat | acataagtta | agcattggtt | atatatagat | 360 |
| attatctcca | atttaagcta | ttaaattgaa | caactattca | aattaattct | ttcagtatt | 420 |
| aattgcagcc | acaatcactt | taaatgcaac | taatccacta | tgaaatgttt | gaacggtaga | 480 |
| tacaaaaaag | ttcaacgtga | cattcactta | ctaatttaat | acctaccaaa | ccctatgtc | 540 |
| cattttttt | aaaaataaaa | taaaattcaa | cttctcattc | attttccttc | tacttcattc | 600 |
| tcactctctc | tatataaaga | aattgtgata | ttgaaaaact | ggatccacaa | tcgaattcgt | 660 |

```
ggtaactttt actcatctcc tccaattatt tctgatttca tgcatgtttc cctacattct    720
attatgaatc gtgttatggt gtataaacgt tgtttcatat ctcatctcat ctattctgat    780
tttgattctc ttgcctactg aatttgaccc tactgtaatc ggtgataaat gtgaatgctt    840
cctcttcttc ttcttcttct cagaaatcaa tttctgtttt gttttgttc atctgtagct     900 tctgcagagt ttttcaatat cacaatttct ttatatagag agagtgagaa tgaagtagaa    960
ggaaaatgaa tgagaagttg aattttattt tattttaaa aaaaatggac ataggggttt     1020
ggtaggtatt aaattagtaa gtgaatgtca cgttgaactt ttttgtatct accgttcaaa    1080
catttcatag tggattagtt gcatttaaag tgattgtggc tgcaattaaa tactgaaaga    1140
attaatttga atagttgttc aatttaatag cttaaattgg agataatatc tatatataac    1200
caatgcttaa cttatgtata ctgacaaaat aataataata atgaatctga cagctattta    1260
tttttatgta aggatccaat tatatttacc cggacaaatg tgggtgtttg ttttgatcg     1320 taaatttcta aagtctcttt ctttcttttt ttctgaaact ttgtgttcag tcaaacatcg    1380
ctacataaat tgaaatagaa attgtactac ttaatagagg gggagaatat tactttgtga    1440
atgaatttat ccaatatttg tattgatgaa aaataacaag tatttcttaa aattaatcaa    1500
aatatgtgta aactgatccg aacataatcg gtaccccaac cccatgg                  1547

<210> SEQ ID NO 12
<211> LENGTH: 187
<212> TYPE: DNA
<213> ORGANISM: Solanum tuberosum

<400> SEQUENCE: 12
gatcctgact cttttacct tcatttctg aaaatggcaa gtgaagttca ttcagttgtt       60
gatgcccatt ctcccccgaa gacgccaacg gtttgcgtca caggagcagc tggatttatc    120
ggctcttggc ttgtcatgag actccttgaa cgcggttata atgtccatgc tactgttcgt    180
gatcctg                                                              187

<210> SEQ ID NO 13
<211> LENGTH: 1335
<212> TYPE: DNA
<213> ORGANISM: Lycopersicon esculentum

<400> SEQUENCE: 13 ctcgagcct ttaaaaagta tagtcaatat ttacggtgac cgtgaatttc ttaattatga      60
tatataattt aaaagaaatc atgatcacat tctactgatg agaacatgtg ctaatcaagg    120
gaaaacatgg atgtgaaaaa tacttttgt taaaagtaaa aaaaaatgtg aattttgtt      180 agttatttac tacctataca ttatttgagc atgtgcaaac tttacaaata cctaatagaa    240
gattttcacc tgcctgtata tatgtaaatt aattataatg aacactctca cataaaataa    300
ttatcagtat atacattaat acttgccctc cacaatgaat taaataaaat gtagaacatg    360
atctacactt caataaaact aagaccataa agaataattt caaaatatac acatgtcaac    420
aataaattat ttgcatatta tattaactta ctaaacaatc tttacttttg aaatataaaa    480
ataatcaagt tataagtctg ctcaaagtaa agcacttgtt agactcatct gattttgaga    540
aggtaagcaa attgatggtg cataatagtc acaagtaaaa tataaatag atttcattag     600 taaaattgtt ttttacttc tttatatata attatcaata tccttcaatg gtaggttaat     660
tatattgtta acttccttgtt gaattaaagc aataagacaa gaatattaaa gataaaagaa    720
```

```
caataaaaat agaaagacta agagataaga gttttcttat tcttctttca ataagtatca        780
tcaagtgtat acaatataaa tttttgtatt tttgatctat ctatttataa tgttatatat        840
aagcatacaa aagatcagtc ataaatatga ctttaatcat gaaaataatg aaagagatta        900
tgaaggcgta aggttactag aataatagtc attaaaaaaa ggggttatct ttataattga        960
ataattgatg aagtaatgga gataattagt gagcataaat tttttaaaa aaatggacat        1020 ttacactata atattttata acactttccc ttaaacatct aggtataaat aatgagtctt       1080
gtcaaaatct tagtaggaaa aattctgtga aattttttta gtgaaaacaa atgatataaa       1140
tatcttgaat actcattatt tgttgtctca ttaaaaatct tatctgacct ataaaataaa       1200
ttatttgctc aactcaaaat agttttcat tctaaaatta gtataattat tagtgaatat       1260
ttaattaaca taattgtata ctaaggggcc tataaattgg attcttctca aagaaaaata       1320
aaatcaccac acaac                                                       1335

<210> SEQ ID NO 14
<211> LENGTH: 1086
<212> TYPE: DNA
<213> ORGANISM: Lycopersicon esculentum

<400> SEQUENCE: 14
tagaaggaat ttcacgaaat cggcccttat tcaaaaataa cttttaaata atgaattta         60 aattttaaga ataatatcc aatgaataaa tgacatgtag cattttacct aaatatttca        120 actatttaa tccatattta atttgtttta ttcccaacaa tagaaagtct tgtgcagaca        180
tttaatctga cttttccagt actaaatatt aattttctga agattttcgg gtttagtcca        240
caagttttag tgagaagttt tgctcaaaat tttaggtgag aaggtttgat atttatcttt        300
tgttaaatta atttatctag gtgactatta tttatttaag tagaaattca tatcattact        360
tttgccaact tgtagtcata ataggagtag gtgtatatga tgaaggaata aacaagttca        420
gtgaagtgat taaaataaaa tataatttag gtgtacatca aataaaaacc ttaaagttta       480
gaaaggcacc gaataatttt gcatagaaga tattagtaaa tttataaaaa taaagaaat        540 gtagttgtca agttgtcttc tttttttgg ataaaaatag cagttggctt atgtcattct        600
tttacaacct ccatgccact tgtccaattg ttgacactta actaattagt ttgattcatg        660
tatgaatact aaataatttt ttaggactga ctcaaatatt tttatattat catagtaata        720
tttatctaat ttttaggacc acttattact aaataataaa ttaactacta ctatattatt        780
gttgtgaaac aacaacgttt tggttgttat gatgaaacgt acactatatc agtatgaaaa        840
attcaaaacg attagtataa attatattga aaatttgata tttttctatt cttaatcaga        900
cgtattgggt ttcatatttt aaaaagggac taaacttaga agagaagttt gtttgaaact        960
acttttgtct ctttcttgtt cccatttctc tcttagattt caaaaagtga actactttat       1020
ctctttcttt gttcacattt tattttattc tattataaat atggcatcct catattgaga       1080
ttttta                                                                 1086

<210> SEQ ID NO 15
<211> LENGTH: 576
<212> TYPE: DNA
<213> ORGANISM: Nicotiana tabacum

<400> SEQUENCE: 15
agtgctcttc cttttctcgc cgctaaatgg aaaagcaaaa gctcagagga gttggctaat         60
tcactcgact ttttcaggga tatcgtcaca ggtcccttg agaaattcac ccgagtgact        120
```

```
atgatcttgc ctttgacggg taagcaatac tcagagaagg tggcagaaaa ttgtgttgcc    180
cattggaaag caataggaac ctacaccgat gcagagagtc aggccattga aaagctcctc    240
aacattttcc agaatgaaac cttcccgccg ggtgcctcca ttcttttac tcaatcacct     300 gttgggcat tgacgattag cttcattaaa gatgattcaa ttactggcac tggaaatgct    360
gttatagaga acaaacaatt gtctgaagca gtgctggaat ccataattgg caaacatgga    420
gtttcccctg cagcaaagtg tagtatcgcc gaaagagtgt caggactatt caaaaagagc    480
tatgccgacg cgtcagtttt tgaaaaacca ggaattgaga atcctccga tccagtgatt    540 gaggagaaac ctaccattcc agaaattgga gtctag                              576

<210> SEQ ID NO 16
<211> LENGTH: 1576
<212> TYPE: DNA
<213> ORGANISM: Solanum tuberosum

<400> SEQUENCE: 16
atgtctcctc cagtgtccgt tactaaaatg caggttgaga attatgtgtt cccaccaaca     60
atggtgaaac ctccgagctc caacaatacg ttttctcctcg ccggcgcagg ttttgttaaa   120 tttttttat aatgtatgat cgaataattt tttatgtgtg tttggtaggc ggcgtaaaac     180
ttgctaattc atgatgaatt tgagtagcag agaattcaat ttgttcaggc tttgttagtt    240
tttgtttagc tggcgtaaaa cttgttaatt catgatgaat tcgagtagca gagaattcaa    300
tttggttagg ttttgttatt ttttaaataa tgtatggttg aataatttct tatgtgtgtg    360
tggtagctgg cgtaaaattt gttaattcat gatgaatttg agtagcagag aattcatttt    420
ggttaggttt tgttattttt ttataatgta tggttaata atttcttatg tgtgtttggt    480
agctggcgta aaacttgtta attcatgatg aattcgagta gcagagaatt caatttggtt    540
aggttttgtt gttttttata atgttgaata aaaaaaatta tgtgtgtctg gtagctagtg    600
taaaacttgt taattcatga tgaattctcg tagtacagaa tccaatttgt ttagttgttg    660
tataatgaat ttaatttcaa tatgtgtggt agggaataga ggtttggaga ttgaaggaaa    720
atttgtgaag tttactgcga tcggcgtgta cttggaagag agtgctattc catttctagc    780
tgataaatgg aaagggaaaa gctctgagga gttgaacat tcagtcgaat tcttcaggga    840
tatcgttaca ggtatttgct gaataggaga attaagctgg ggtttatcat ataagatgct    900
aagtatttag ggtcttaaaa caatcaagag atttgtttcc atcaaagtta acgtttgtga    960
atattttcat cttccctctc tggtaggtcc ctttgagaaa ttcactcgag tgactatgat   1020
cttgcccttg acgggtaagc aatactctga gaaggtggca gaaattgtg ttgcctattg    1080 gaaagcaata ggaacctaca gtgatgcaga gagggaggcc attgaaaagt tcctcaatgt   1140
tttccagagt gaaaccttcc cacctggtgc ctccatcatt tttactcaat accgcttgg    1200 atcattgacg gtatgtatat caactatatt gaacgataac aaaaaaaaat gggcacttgc   1260
aagttgcatc atcgattagg acccttggaa caatatttgt gcaccaaaaa atgaattgc    1320 atttatctat aagctcattg atgtttcttc tatatatttt ttgtccgagt ccagattagc    1380
ttctctaaag atgattctgt tccttgcgtt gggaatgctg ttatagagaa caaacaattg   1440
tcagaagcag tgctggattc cataattggc gagcacggag tttcccttgc agcaaagtgt   1500
agtattgcca aaagagtatc agaactgttg gtttgtgaaa agccaggaag tgagctatcc   1560
tcagtccagt aactag                                                   1576
```

```
<210> SEQ ID NO 17
<211> LENGTH: 274
<212> TYPE: PRT
<213> ORGANISM: Lycopersicon esculentum

<400> SEQUENCE: 17

Met Asn Ser Thr Ser Met Ser Ser Leu Gly Val Arg Lys Gly Ser Trp
 1               5                  10                  15

Thr Asp Glu Glu Asp Phe Leu Leu Arg Lys Cys Ile Asp Lys Tyr Gly
             20                  25                  30

Glu Gly Lys Trp His Leu Val Pro Ile Arg Ala Gly Leu Asn Arg Cys
         35                  40                  45

Arg Lys Ser Cys Arg Leu Arg Trp Leu Asn Tyr Leu Arg Pro His Ile
     50                  55                  60

Lys Arg Gly Asp Phe Glu Gln Asp Glu Val Asp Leu Ile Leu Arg Leu
 65                  70                  75                  80

His Lys Leu Leu Gly Asn Arg Trp Ser Leu Ile Ala Gly Arg Leu Pro
                 85                  90                  95

Gly Arg Thr Ala Asn Asp Val Lys Asn Tyr Trp Asn Thr Asn Leu Leu
            100                 105                 110

Arg Lys Leu Asn Thr Thr Lys Ile Val Pro Arg Glu Lys Ile Asn Asn
        115                 120                 125

Lys Cys Gly Glu Ile Ser Thr Lys Ile Glu Ile Ile Lys Pro Gln Arg
    130                 135                 140

Arg Lys Tyr Phe Ser Ser Thr Met Lys Asn Val Thr Asn Asn Asn Val
145                 150                 155                 160

Ile Leu Asp Glu Glu Glu His Cys Lys Glu Ile Ile Ser Glu Lys Gln
                165                 170                 175

Thr Pro Asp Ala Ser Met Asp Asn Val Asp Pro Trp Trp Ile Asn Leu
            180                 185                 190

Leu Glu Asn Cys Asn Asp Asp Ile Glu Glu Asp Glu Val Val Ile
        195                 200                 205

Asn Tyr Glu Lys Thr Leu Thr Ser Leu Leu His Glu Glu Ile Ser Pro
    210                 215                 220

Pro Leu Asn Ile Gly Glu Gly Asn Ser Met Gln Gln Gly Gln Ile Ser
225                 230                 235                 240

His Glu Asn Trp Gly Glu Phe Ser Leu Asn Leu Pro Pro Met Gln Gln
                245                 250                 255

Gly Val Gln Asn Asp Asp Phe Ser Ala Glu Ile Asp Leu Trp Asn Leu
            260                 265                 270

Leu Asp

<210> SEQ ID NO 18
<211> LENGTH: 259
<212> TYPE: PRT
<213> ORGANISM: Solanum tuberosum

<400> SEQUENCE: 18

Lys Gly Ser Trp Thr Glu Gln Glu Asp Phe Leu Leu Arg Lys Cys Ile
 1               5                  10                  15

Gln Ile Tyr Gly Glu Gly Lys Trp His Leu Val Pro Ala Arg Ala Gly
             20                  25                  30

Leu Asn Arg Cys Arg Lys Ser Cys Arg Leu Arg Trp Leu Asn Tyr Leu
         35                  40                  45

Arg Pro His Ile Lys Arg Gly Asp Phe Ala Pro Asp Glu Val Asp Leu
```

-continued

```
                    50                  55                  60
Ile Leu Arg Leu His Lys Leu Leu Gly Asn Arg Trp Ser Leu Ile Ala
 65                  70                  75                  80

Gly Arg Leu Pro Gly Arg Thr Ala Asn Asp Val Lys Asn Tyr Trp Asn
                 85                  90                  95

Thr His Phe Gln Lys Leu Asn Ile Ile Thr Pro Pro Arg Pro
            100                 105                 110

Arg Pro Asn Pro His Leu His Ile Lys His Lys Ser Ile Val Val Thr
            115                 120                 125

Lys Asn Glu Ile Ile Arg Pro Gln Pro Arg Asn Phe Ser Asn Val Lys
        130                 135                 140

Lys Asn Asn Ser His Trp Cys Asn Asn Lys Ser Met Ile Thr Asn Thr
145                 150                 155                 160

Leu Asp Lys Asp Asp Lys Arg Cys Lys Glu Ile Val Val Asn Ile Ser
                165                 170                 175

Glu Lys Pro Thr Arg Glu Asn Thr Ser Ser Ile Asp Asp Gly Val Gln
            180                 185                 190

Trp Trp Thr Asn Leu Leu Glu Asn Cys Asn Glu Ile Glu Glu Glu Val
        195                 200                 205

Ala Val Thr Asn Phe Glu Lys Thr Pro Thr Met Leu Leu His Glu Glu
        210                 215                 220

Ile Ser Pro Pro Leu Ile Asn Gly Glu Gly Asn Ser Met Gln Gln Gly
225                 230                 235                 240

Gln Ser His Asp Trp Asp Asp Phe Ser Thr Asp Ile Asp Leu Trp Asn
                245                 250                 255

Leu Leu Asn

<210> SEQ ID NO 19
<211> LENGTH: 256
<212> TYPE: PRT
<213> ORGANISM: Solanum tuberosum

<400> SEQUENCE: 19

Thr Pro Met Met Cys Thr Ser Leu Gly Val Ile Arg Lys Gly Ser Trp
  1               5                  10                  15

Thr Glu Glu Asp Ile Leu Arg Lys Cys Ile Asp Lys Tyr Gly
            20                  25                  30

Glu Gly Lys Trp Asn Leu Val Pro Thr Arg Ala Gly Leu Asn Arg Cys
         35                  40                  45

Arg Lys Ser Cys Arg Leu Arg Trp Leu Asn Tyr Leu Arg Pro His Ile
     50                  55                  60

Lys Arg Gly Asp Phe Asp Trp Asp Glu Val Asp Leu Ile Leu Arg Leu
 65                  70                  75                  80

His Lys Leu Leu Gly Asn Arg Trp Ser Leu Ile Ala Gly Arg Leu Pro
                 85                  90                  95

Gly Arg Thr Ala Asn Asp Val Lys Asn Tyr Trp Asn Thr Asn Leu Leu
            100                 105                 110

Arg Lys Leu Asn Thr Ser Thr Lys Phe Ala Pro Gln Pro Gln Glu Gly
        115                 120                 125

Ile Asn Thr Ser Thr Ile Ala Pro Gln Pro Gln Glu Gly Ile Lys Cys
    130                 135                 140

Gly Lys Ala Asn Ala Ile Ile Arg Pro Gln Pro Gln Lys Phe Arg Ser
145                 150                 155                 160

Ser Met Lys Ile Asn Val Ser Trp Cys Asn Asn Asn Ser Ile Val Asn
```

-continued

```
                165                 170                 175
Asn Glu Glu Ala Ser Lys Asp Asn Asn Asp Met Gln Trp Trp Ala Asn
            180                 185                 190

Ile Leu Glu Asn Cys Asn Asp Ile Gly Glu Gly Glu Ala Glu Arg Thr
            195                 200                 205

Leu Pro Ser Cys Lys Glu Ile Asn Cys Asn Glu Ile Asp Lys Thr Pro
            210                 215                 220

Ser Leu Leu His Asp Gly Asn Ser Thr Gln Gln Gly Gln Gly Asp
225                 230                 235                 240

Gly Gly Trp Asp Glu Phe Ser Leu Asp Asp Ile Trp Asn Leu Leu Asn
            245                 250                 255

<210> SEQ ID NO 20
<211> LENGTH: 262
<212> TYPE: PRT
<213> ORGANISM: Capsicum annuum

<400> SEQUENCE: 20

Met Asn Thr Ala Ile Ile Ala Lys Ser Ser Gly Val Arg Lys Gly Ala
1               5                   10                  15

Trp Thr Glu Glu Asp Phe Leu Leu Arg Lys Cys Ile Gln Asn Tyr
            20                  25                  30

Gly Glu Gly Lys Trp His Leu Val Pro Ile Arg Ala Gly Leu Asn Arg
        35                  40                  45

Cys Arg Lys Ser Cys Arg Leu Arg Trp Leu Asn Tyr Leu Arg Pro His
    50                  55                  60

Ile Lys Arg Gly Asp Phe Gly Trp Asp Glu Ile Asp Leu Ile Leu Arg
65                  70                  75                  80

Leu His Lys Leu Leu Gly Asn Arg Trp Ser Leu Ile Ala Gly Arg Leu
                85                  90                  95

Pro Gly Arg Thr Ala Asn Asp Val Lys Asn Tyr Trp Asn Ser His Leu
            100                 105                 110

Gln Lys Lys Leu Ile Thr Ala Pro His Arg Gln Glu Lys Lys Tyr Asn
        115                 120                 125

Thr Ala Leu Lys Ile Thr Thr Lys Asn Val Leu Arg Pro Arg Pro Arg
    130                 135                 140

Thr Phe Ser Ser Ser Ala Lys Asn Asn Ile Ser Trp Cys Thr Asn Lys
145                 150                 155                 160

Ser Thr Val Ile Thr Asn Thr Leu Asp Lys Asp Glu Arg Asp Lys Glu
                165                 170                 175

Ile Gly Leu Asn Ile Cys Gln Lys Leu Thr Ser Glu Thr Ser Ser Thr
            180                 185                 190

Ile Asp Asp Gly Val Gln Trp Trp Thr Ser Leu Leu Glu Asn Cys Lys
        195                 200                 205

Glu Ile Glu Glu Asp Val Ala Ala Val Gly Ile Phe Glu Glu Lys Asn
    210                 215                 220

Lys Leu Val Pro Ser Leu Leu His Asp Glu Ile Asn Ser Leu Thr Met
225                 230                 235                 240

Gln Gln Gly Gln Ser Asp Gly Trp Asp Phe Ser Ala Asp Ile Asp
                245                 250                 255

Leu Trp Asn Leu Leu Asn
            260

<210> SEQ ID NO 21
<211> LENGTH: 255
```

```
<212> TYPE: PRT
<213> ORGANISM: Petunia hybrida

<400> SEQUENCE: 21

Met Ser Thr Ser Asn Ala Ser Thr Ser Gly Val Arg Lys Gly Ala Trp
  1               5                  10                  15

Thr Glu Glu Glu Asp Leu Leu Arg Glu Cys Ile Asp Lys Tyr Gly
                 20                  25                  30

Glu Gly Lys Trp His Leu Val Pro Val Arg Ala Gly Leu Asn Arg Cys
             35                  40                  45

Arg Lys Ser Cys Arg Leu Arg Trp Leu Asn Tyr Leu Arg Pro His Ile
 50                  55                  60

Lys Arg Gly Asp Phe Ser Leu Asp Glu Val Asp Leu Ile Leu Arg Leu
 65                  70                  75                  80

His Lys Leu Leu Gly Asn Arg Trp Ser Leu Ile Ala Gly Arg Leu Pro
                 85                  90                  95

Gly Arg Thr Ala Asn Asp Val Lys Asn Tyr Trp Asn Thr His Leu Arg
            100                 105                 110

Lys Lys Leu Ile Ala Pro His Asp Gln Lys Gln Glu Ser Lys Asn Lys
        115                 120                 125

Ala Val Lys Ile Thr Glu Asn Asn Ile Ile Lys Pro Arg Pro Arg Thr
130                 135                 140

Phe Ser Arg Pro Ala Met Asn Asn Phe Pro Cys Trp Asn Gly Lys Ser
145                 150                 155                 160

Cys Asn Lys Asn Thr Ile Asp Lys Asn Glu Gly Asp Thr Glu Ile Ile
                165                 170                 175

Lys Phe Ser Asp Glu Lys Gln Lys Pro Glu Glu Ser Ile Asp Asp Gly
            180                 185                 190

Leu Gln Trp Trp Ala Asn Leu Leu Ala Asn Asn Ile Glu Ile Glu Glu
        195                 200                 205

Leu Val Ser Cys Asn Ser Pro Thr Leu Leu His Glu Glu Thr Ala Pro
210                 215                 220

Ser Val Asn Ala Glu Ser Ser Leu Thr Gln Gly Gly Gly Ser Gly Leu
225                 230                 235                 240

Ser Asp Phe Ser Val Asp Ile Asp Ile Trp Asp Leu Val Ser
                245                 250                 255

<210> SEQ ID NO 22
<211> LENGTH: 247
<212> TYPE: PRT
<213> ORGANISM: Vitis sp.

<400> SEQUENCE: 22

Met Glu Ser Leu Gly Val Arg Lys Gly Ala Trp Ile Gln Glu Glu Asp
  1               5                  10                  15

Val Leu Leu Arg Lys Cys Ile Glu Lys Tyr Gly Glu Gly Lys Trp His
                 20                  25                  30

Leu Val Pro Leu Arg Ala Gly Leu Asn Arg Cys Arg Lys Ser Cys Arg
             35                  40                  45

Leu Arg Trp Leu Asn Tyr Leu Lys Pro Asp Ile Lys Arg Gly Glu Phe
 50                  55                  60

Ala Leu Asp Glu Val Asp Leu Met Ile Arg Leu His Asn Leu Leu Gly
 65                  70                  75                  80

Asn Arg Trp Ser Leu Ile Ala Gly Arg Leu Pro Gly Arg Thr Ala Asn
                 85                  90                  95
```

```
Asp Val Lys Asn Tyr Trp His Gly His His Leu Lys Lys Lys Val Gln
                100                 105                 110

Phe Gln Glu Glu Gly Arg Asn Lys Pro Leu Thr His Ser Lys Thr Lys
            115                 120                 125

Ala Ile Lys Pro His Pro His Lys Phe Ser Lys Ala Leu Pro Arg Phe
        130                 135                 140

Glu Leu Lys Thr Thr Ala Val Asp Thr Phe Asp Thr Gln Val Ser Thr
145                 150                 155                 160

Ser Ser Lys Pro Ser Ser Thr Ser Pro Gln Pro Asn Asp Asp Ile Ile
                165                 170                 175

Trp Trp Glu Ser Leu Leu Ala Glu Leu Asp Gln Glu Thr Asp Phe Ser
            180                 185                 190

Ala Ser Gly Glu Met Leu Ile Ala Ser Leu Arg Ala Glu Glu Thr Ala
        195                 200                 205

Thr Gln Lys Lys Gly Pro Met Asp Gly Met Ile Glu Gln Ile Gln Gly
    210                 215                 220

Gly Glu Gly Asp Phe Pro Phe Asp Val Gly Phe Trp Asp Thr Pro Asn
225                 230                 235                 240

Thr Gln Val Asn His Leu Ile
                245

<210> SEQ ID NO 23
<211> LENGTH: 272
<212> TYPE: PRT
<213> ORGANISM: Ipomoea purpurea

<400> SEQUENCE: 23

Met Val Asn Ser Ser Ala Arg Trp Ser Pro Arg Val Arg Lys Gly Ala
1               5                   10                  15

Trp Ser Glu Glu Glu Asp Asp Leu Leu Arg Lys Cys Ile Gln Lys Phe
            20                  25                  30

Gly Glu Gly Lys Trp His Leu Val Pro Phe Arg Ala Gly Leu Asn Arg
        35                  40                  45

Cys Arg Lys Ser Cys Arg Leu Arg Trp Leu Asn Tyr Leu His Pro Asp
    50                  55                  60

Ile Lys Arg Gly His Phe Ser Leu Glu Glu Ala Asp Leu Ile Leu Arg
65                  70                  75                  80

Leu His Lys Leu Leu Gly Asn Arg Trp Ser Leu Ile Ala Gly Arg Ile
                85                  90                  95

Pro Gly Arg Thr Ala Asn Asp Val Lys Asn Tyr Trp His Ser His Leu
            100                 105                 110

Lys Lys Lys Val Val Ser Met His Met Ala Ser Ser Asn Ser Ser Arg
        115                 120                 125

Gln Asp Asn Asn Trp Asp Asp Glu Lys Gly Lys Ala Pro Gln Ile Lys
    130                 135                 140

Glu Asn Ile Leu Phe Arg Pro Arg Pro Arg Phe Phe Arg Thr Ser
145                 150                 155                 160

Leu Ser Ser Pro Ala Leu Ser Thr Leu Thr Gly Lys Ala Lys Ala Val
                165                 170                 175

Val Tyr Asp Ala Pro Pro Pro Pro Pro Pro His Gln Leu Gln
            180                 185                 190

Pro Gln Pro Glu Ala Thr Ser Pro Ala Ala Asp Leu Leu Met Val Phe
        195                 200                 205

Asn Val Gln Gln Asn Ser Asn Ser Ile Glu Thr Asn Leu Pro Ala Gln
    210                 215                 220
```

```
Thr Thr Ala Pro Ser Ser His Asp Gly Val Lys Trp Trp Glu Asp Leu
225                 230                 235                 240

Leu Tyr Asp Asp Ser His Gln Gly Leu Ile Asp Trp Thr Thr Asp Asp
            245                 250                 255

Asp Phe Pro Ile Asp Val Thr Leu Leu Lys Leu Leu Asp Thr Thr Ile
            260                 265                 270

<210> SEQ ID NO 24
<211> LENGTH: 194
<212> TYPE: PRT
<213> ORGANISM: Antirrhinum majus

<400> SEQUENCE: 24

Met Gly Asn Asn Pro Leu Gly Val Arg Lys Gly Thr Trp Thr Lys Glu
1               5                   10                  15

Glu Asp Ile Leu Leu Lys Gln Cys Ile Glu Lys Tyr Gly Glu Gly Lys
            20                  25                  30

Trp His Gln Val Pro Ile Arg Ala Gly Leu Asn Arg Cys Arg Lys Ser
        35                  40                  45

Cys Arg Met Arg Trp Leu Asn Tyr Leu Ser Pro Asn Ile Lys Arg Gly
50                  55                  60

Ser Phe Thr Arg Asp Glu Val Asp Leu Ile Val Arg Leu His Lys Leu
65                  70                  75                  80

Leu Gly Asn Arg Trp Ser Leu Ile Ala Gly Arg Leu Pro Gly Arg Thr
                85                  90                  95

Gly Asn Asp Val Lys Asn Phe Trp Asn Thr His Phe Glu Lys Lys Ser
            100                 105                 110

Gly Glu Arg Glu Asn Thr Glu Asn Ile Asn Pro Lys Leu Ile Asn Ser
        115                 120                 125

Ser Asn Ile Ile Lys Pro Gln Pro Arg Thr Phe Leu Lys Leu Arg Pro
    130                 135                 140

Lys Glu Thr Lys Lys Gln Lys Asn Ile Arg Asn Val Cys Thr Ala Asn
145                 150                 155                 160

Asp Asp Lys Gln Gln Pro Leu Ser Thr Ser Gly Gln Leu Glu Glu Val
                165                 170                 175

Asn Glu Arg Ile Arg Trp Trp Ser Glu Leu Leu Asp Phe Ala Asp Tyr
            180                 185                 190

Val Asp

<210> SEQ ID NO 25
<211> LENGTH: 248
<212> TYPE: PRT
<213> ORGANISM: Arabidopsis thaliana

<400> SEQUENCE: 25

Met Glu Gly Ser Ser Lys Gly Leu Arg Lys Gly Ala Trp Thr Thr Glu
1               5                   10                  15

Glu Asp Ser Leu Leu Arg Gln Cys Ile Asn Lys Tyr Gly Glu Gly Lys
            20                  25                  30

Trp His Gln Val Pro Val Arg Ala Gly Leu Asn Arg Cys Arg Lys Ser
        35                  40                  45

Cys Arg Leu Arg Trp Leu Asn Tyr Leu Lys Pro Ser Ile Lys Arg Gly
50                  55                  60

Lys Leu Ser Ser Asp Glu Val Asp Leu Leu Leu Arg Leu His Arg Leu
65                  70                  75                  80
```

```
Leu Gly Asn Arg Trp Ser Leu Ile Ala Gly Arg Leu Pro Gly Arg Thr
            85                  90                  95

Ala Asn Asp Val Lys Asn Tyr Trp Asn Thr His Leu Ser Lys Lys His
            100                 105                 110

Glu Pro Cys Cys Lys Ile Lys Met Lys Lys Arg Asp Ile Thr Pro Ile
        115                 120                 125

Pro Thr Thr Pro Ala Leu Lys Asn Asn Val Tyr Lys Pro Arg Pro Arg
    130                 135                 140

Ser Phe Thr Val Asn Asn Asp Cys Asn His Leu Asn Ala Pro Pro Lys
145                 150                 155                 160

Val Asp Val Asn Pro Pro Cys Leu Gly Leu Asn Ile Asn Asn Val Cys
                165                 170                 175

Asp Asn Ser Ile Ile Tyr Asn Lys Asp Lys Lys Lys Asp Gln Leu Val
            180                 185                 190

Asn Asn Leu Ile Asp Gly Asp Asn Met Trp Leu Glu Lys Phe Leu Glu
        195                 200                 205

Glu Ser Gln Glu Val Asp Ile Leu Val Pro Glu Ala Thr Thr Thr Glu
    210                 215                 220

Lys Gly Asp Thr Leu Ala Phe Asp Val Asp Gln Leu Trp Ser Leu Phe
225                 230                 235                 240

Asp Gly Glu Thr Val Lys Phe Asp
                245

<210> SEQ ID NO 26
<211> LENGTH: 266
<212> TYPE: PRT
<213> ORGANISM: Zea mays

<400> SEQUENCE: 26

Met Gly Arg Arg Ala Cys Cys Ala Lys Glu Gly Val Lys Arg Gly Ala
1               5                   10                  15

Trp Thr Ala Lys Glu Asp Asp Thr Leu Ala Ala Tyr Val Lys Ala His
            20                  25                  30

Gly Glu Gly Lys Trp Arg Glu Val Pro Gln Lys Ala Gly Leu Arg Arg
        35                  40                  45

Cys Gly Lys Ser Cys Arg Leu Arg Trp Leu Asn Tyr Leu Arg Pro Asn
    50                  55                  60

Ile Lys Arg Gly Asn Ile Ser Tyr Asp Glu Glu Asp Leu Ile Val Arg
65                  70                  75                  80

Leu His Lys Leu Leu Gly Asn Arg Trp Ser Leu Ile Ala Gly Arg Leu
            85                  90                  95

Pro Gly Arg Thr Asp Asn Glu Ile Lys Asn Tyr Trp Asn Ser Thr Leu
        100                 105                 110

Gly Arg Arg Ala Gly Ala Ala Gly Ala Ser Arg Val Val Phe Ala Pro
    115                 120                 125

Asp Thr Gly Ser His Ala Thr Pro Ala Ala Ser Gly Ser Arg Glu Met
130                 135                 140

Thr Gly Gly Gln Lys Gly Ala Ala Pro Arg Ala Asp Leu Gly Ser Pro
145                 150                 155                 160

Gly Ser Ala Ala Val Val Trp Ala Pro Lys Ala Ala Arg Cys Thr Gly
                165                 170                 175

Gly Leu Phe Phe His Arg Asp Thr Pro His Ala Gly Glu Thr Glu Thr
            180                 185                 190

Pro Thr Pro Met Met Met Ala Gly Gly Gly Gly Glu Ala Arg Ser
        195                 200                 205
```

```
Ser Asp Asp Cys Ser Ser Ala Ala Ser Val Ser Pro Leu Val Gly Ser
    210                 215                 220

Ser Gln His Asp Pro Cys Phe Ser Gly Asp Gly Asp Gly Asp Trp Met
225                 230                 235                 240

Asp Asp Val Arg Ala Leu Ala Ser Phe Leu Glu Ser Asp Glu Glu Trp
                245                 250                 255

Leu Arg Cys His Thr Ala Glu Gln Leu Val
            260                 265

<210> SEQ ID NO 27
<211> LENGTH: 258
<212> TYPE: PRT
<213> ORGANISM: Arabidopsis thaliana

<400> SEQUENCE: 27

Met Gly Lys Arg Ala Thr Thr Ser Val Arg Arg Glu Glu Leu Asn Arg
  1               5                  10                  15

Gly Ala Trp Thr Asp His Glu Asp Lys Ile Leu Arg Asp Tyr Ile Thr
             20                  25                  30

Thr His Gly Glu Gly Lys Trp Ser Thr Leu Pro Asn Gln Ala Gly Leu
         35                  40                  45

Lys Arg Cys Gly Lys Ser Cys Arg Leu Arg Trp Lys Asn Tyr Leu Arg
 50                  55                  60

Pro Gly Ile Lys Arg Gly Asn Ile Ser Ser Asp Glu Glu Glu Leu Ile
 65                  70                  75                  80

Ile Arg Leu His Asn Leu Leu Gly Asn Arg Trp Ser Leu Ile Ala Gly
                 85                  90                  95

Arg Leu Pro Gly Arg Thr Asp Asn Glu Ile Lys Asn His Trp Asn Ser
            100                 105                 110

Asn Leu Arg Lys Arg Leu Pro Lys Thr Gln Thr Lys Gln Pro Lys Arg
        115                 120                 125

Ile Lys His Ser Thr Asn Asn Glu Asn Asn Val Cys Val Ile Arg Thr
130                 135                 140

Lys Ala Ile Arg Cys Ser Lys Thr Leu Leu Phe Ser Asp Leu Ser Leu
145                 150                 155                 160

Gln Lys Lys Ser Ser Thr Ser Pro Leu Pro Leu Lys Glu Gln Glu Met
                165                 170                 175

Asp Gln Gly Gly Ser Ser Leu Met Gly Asp Leu Glu Phe Asp Phe Asp
            180                 185                 190

Arg Ile His Ser Glu Phe His Phe Pro Asp Leu Met Asp Phe Asp Gly
        195                 200                 205

Leu Asp Cys Gly Asn Val Thr Ser Leu Val Ser Ser Asn Glu Ile Leu
210                 215                 220

Gly Glu Leu Val Pro Ala Gln Gly Asn Leu Asp Leu Asn Arg Pro Phe
225                 230                 235                 240

Thr Ser Cys His His Arg Gly Asp Asp Glu Asp Trp Leu Arg Asp Phe
                245                 250                 255

Thr Cys
```

HIGH LEVEL ANTIOXIDANT-CONTAINING FOODS

This U.S. non-provisional application claims priority to U.S. provisional application Ser. No. 60/818,516, which was filed on Jul. 6, 2006, and which is incorporated herein by reference in its entirety.

FIELD OF THE INVENTION

The present invention relates to modifying the level of at least one antioxidant in a crop or plant or any product of a crop or plant. Particularly, the present invention modifies the level of at least one polyphenolic compound in a plant or product thereof by modifying the expression of a chlorogenic acid-inducing (Cai) gene. Furthermore, the present invention boosts antioxidant levels by modifying the expression of at least one of the flavanone-3',5'-hydroxylase (F35h) gene, a flavanone-3'-hydroxylase (F3h), a dihydroflavonol reductase (Dfr) gene, and a chalcone isomerase (Chi) gene, in addition to expression of the Cai gene. Antioxidant levels also can be modified according to the present invention by expressing one or more of these genes without necessarily co-expressing the Cai gene.

BACKGROUND

Oxygen is a highly reactive molecular species. Unchecked, it can damage tissues, cells, proteins, and DNA and trigger a cascade of dangerous downstream chain reactions that can culminate in cell death and increased oxidative stress in particular tissues.

But reactive oxygen species do not go unchecked. Living organisms have evolved a vast network of complex antioxidants that counterbalance oxidative-induced molecular destruction by, for example, decreasing localized concentrations of un-reactive oxygen or by scavenging free radicals that would otherwise promote formation of highly reactive species.

Many green vegetables, fruits, plants, and crops are known to produce a myriad different antioxidants. Accordingly, to push the balance of competing oxidative interests more toward the antioxidant side of the equation, and thereby promote a healthy condition, it is thought to be desirable to eat antioxidant-rich plant products or to augment in vivo antioxidant levels by regularly taking appropriate dietary supplements.

Since oxidative stress typically is associated with the pathogenesis of a variety of diseases, such as Parkinson's disease, Alzheimer's disease, diabetes, rheumatoid arthritis, cardiovascular diseases, and neurodegeneration, it also is thought desirable to ingest antioxidants to combat or minimize the damaging effects of those diseases on the body.

A problem is that there do not exist many plants, vegetables, fruits, or products thereof that are naturally highly rich in antioxidants. Furthermore, when those plants and products are processed and cooked, the levels of antioxidants that ultimately remain in the foodstuff is severely undercut. Moreover, what little antioxidant remains available in the food still has to be timely absorbed into the body. Accordingly, the absence of a large reservoir of antioxidants in the starting plant material is detrimental to the overall concept of antioxidant-induced health and disease resistance vigor.

The present invention provides a genetic approach to solving this problem. Genetically modified potato plants of the present invention produce tubers with highly increased levels of at least one antioxidant.

SUMMARY OF THE INVENTION

One aspect of the present invention, therefore, is a method for increasing the level of an antioxidant in a plant, comprising transforming a plant to overexpress (i) a chlorogenic acid-inducing gene (Cai) or (ii) a polynucleotide encoding a protein that shares at least 90% sequence identity with the protein sequence of the Cai gene, in a plant or plant product, wherein the level of the antioxidant, chlorogenic acid, is increased in the transformed plant or its product compared to the level of chlorogenic acid in a non-transformed plant or product thereof. In one embodiment, the Cai gene expresses a protein that shares at least 90% sequence identity to the sequence of SEQ ID NO: 5.

Other embodiments of the present invention include co-expressing the Cai or Cai-related gene with a nucleic acid that brings about the downregulation or inhibition of an endogenous gene involved in a biosynthetic pathway. That then results in accumulation of a particular antioxidant because the protein or enzyme that would normally convert that substance to the next one in the pathway is no longer expressed. Accordingly, depending on which gene in a particular pathway is downregulated or switched off, different antioxidants can be made to accumulate in the plant.

Accordingly, with that in mind, in one embodiment this method further comprises co-transforming the Cai-expressing plant with a construct that expresses a polynucleotide that brings about downregulation or inhibition of endogenous F35h gene expression in the transformed plant or in its product, wherein the plant or product that is co-transformed with the F35h gene has increased levels of the antioxidant, kaempferol, after the F35h gene is downregulated or inhibited.

In another embodiment, the method further comprises co-transforming the Cai-expressing plant with a construct that expresses a polynucleotide that brings about downregulation or inhibition of endogenous Chi gene expression in the transformed plant or its product, wherein the plant or product that is co-transformed with the Chi gene has increased levels of the antioxidant, chalcone, after the Chi gene is downregulated or inhibited.

In another embodiment, the method further comprises co-transforming the Cai-expressing plant with a construct that expresses a polynucleotide that modifies the expression of any endogenous flavonoid pathway gene in the transformed plant or its product, wherein the transformed plant or its product has increased antioxidant levels.

In one embodiment of the present invention, a plant that may be transformed and co-transformed according to any of the present methods is a solanaceous crop plant. In one embodiment, the solanaceous crop plant is a potato plant, a tobacco plant, a tomato plant, a *capsicum* plant, or an eggplant.

In another embodiment, the plant is a cruciferous vegetable. In one embodiment, the cruciferous vegetable is kale, collards, Chinese broccoli (gai laan), cabbage, brussel sprout, kohlrabi, cauliflower, wild broccoli, broccoli, bok choy, mizuna, flowering cabbage, Chinese cabbage, napa cabbage, turnip root, rutabaga, Siberian kale, canola/rape seeds, wrapped heart mustard cabbage, mustard seeds, tatsoi, Ethiopian mustard, radish, daikon, horseradish, Japanese horseradish (wasabi), arugula, watercress, or cress.

In another embodiment, the plant is a tea plant. In one embodiment, the tea plant is a black tea plant, a green tea plant, or a white tea plant.

Another aspect of the present invention is a method for increasing the level of an antioxidant in a plant, comprising expressing in a plant (A) a Cai gene or a polynucleotide that encodes a protein that shares at least 90% sequence identity with the protein encoded by the Cai gene, and (B) a nucleic acid that downregulates or inhibits the endogenous expression of at least one of (i) the F35h gene, (ii) the F3h gene, (iii) the Dfr gene, and (iv) the Chi gene, wherein the level of antioxidants in the plant expressing (A) and (B) is increased compared to a plant that does not express (A) and (B). In one embodiment, the Cai gene expresses a protein that shares at least 90% sequence identity to the sequence of SEQ ID NO: 5.

Another aspect of the present invention is a transformed plant, comprising in its genome (A) a Cai gene or a polynucleotide that encodes a protein that shares at least 90% sequence identity with the protein encoded by the Cai gene, and (B) a nucleic acid that downregulates or inhibits the endogenous expression of at least one of (i) the F35h gene, (ii) the F3h gene, (iii) the Dfr gene, and (iv) the Chi gene.

In one embodiment of the present invention, a plant that may be transformed and co-transformed according to any of the present methods is a solanaceous crop plant. In one embodiment, the solanaceous crop plant is a potato plant, a tobacco plant, a tomato plant, a *capsicum* plant, or an eggplant. In another embodiment, the solanaceous crop plant is any wild species, such as *Solanum phureja*.

In another embodiment, the plant is a cruciferous vegetable. In one embodiment, the cruciferous vegetable is kale, collards, Chinese broccoli (gai laan), cabbage, brussel sprout, kohlrabi, cauliflower, wild broccoli, broccoli, bok choy, mizuna, flowering cabbage, Chinese cabbage, napa cabbage, turnip root, rutabaga, Siberian kale, canola/rape seeds, wrapped heart mustard cabbage, mustard seeds, tatsoi, Ethiopian mustard, radish, daikon, horseradish, Japanese horseradish (wasabi), arugula, watercress, or cress.

In another embodiment, the plant is a tea plant. In one embodiment, the tea plant is a black tea plant, a green tea plant, or a white tea plant.

Another aspect of the present invention is a plant product that is obtained from or made from any of the transformed plants produced from any method of the present invention. A plant product may be, but is not limited to a vegetable, fruit, root, tuber, stem, stalk, leaf, or flower. A product includes any foodstuff or drink that is made from the plant or any one or combination of products. In the case of a tuber, such as a potato, turnip, parsnip, cassava, rutabagas, for instance, a plant product may be the tuber itself or fries, chips, and crisps made from it. The present invention is not limited to these exemplary types of tuber-related food products.

According to the present invention, a plant product has increased levels of at least two of chlorogenic acid, kaempferol, and chalcone compared to a product that is not obtained from the transformed plant.

In another embodiment, the plant product is a potato that has increased levels of at least two of chlorogenic acid, kaempferol, and chalcone compared to a potato that is not obtained from the transformed plant.

In another embodiment, the plant product is a tomato that has increased levels of at least two of chlorogenic acid, kaempferol, and chalcone compared to a tomato that is not obtained from the transformed plant.

In another embodiment, the product is a *capsicum* product that has increased levels of at least two of chlorogenic acid, kaempferol, and chalcone compared to a *capsicum* product that is not obtained from the transformed plant.

In one embodiment, a plant or product that is obtained from or made from any one of the plants transformed by any one of the present inventive methods, has at least about a 1-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 26-fold, 27-fold, 28-fold, 29-fold, 30-fold, 31-fold, 32-fold, 33-fold, 34-fold, 35-fold, 36-fold, 37-fold, 38-fold, 39-fold, 40-fold, 41-fold, 42-fold, 43-fold, 44-fold, 45-fold, 46-fold, 47-fold, 48-fold, 49-fold, 50-fold, 51-fold, 52-fold, 53-fold, 54-fold, 55-fold, 56-fold, 57-fold, 58-fold, 59-fold, 60-fold, 65-fold, 70-fold, 75-fold, 80-fold, 85-fold, 90-fold, 95-fold, 100-fold, 110-fold, 120-fold, 130-fold, 140-fold, 150-fold, 160-fold, 170-fold, 180-fold, 190-fold, 200-fold, or more than 200-fold increase in the level of an antioxidant compared to the level of that same antioxidant from an equivalent product that is obtained from a non-transformed plant of the same species.

In one embodiment, a plant or product is that is obtained from or made from any one of the plants transformed by any one of the present inventive methods, has at least about a 1-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 26-fold, 27-fold, 28-fold, 29-fold, 30-fold, 31-fold, 32-fold, 33-fold, 34-fold, 35-fold, 36-fold, 37-fold, 38-fold, 39-fold, 40-fold, 41-fold, 42-fold, 43-fold, 44-fold, 45-fold, 46-fold, 47-fold, 48-fold, 49-fold, 50-fold, 51-fold, 52-fold, 53-fold, 54-fold, 55-fold, 56-fold, 57-fold, 58-fold, 59-fold, 60-fold, 65-fold, 70-fold, 75-fold, 80-fold, 85-fold, 90-fold, 95-fold, 100-fold, 110-fold, 120-fold, 130-fold, 140-fold, 150-fold, 160-fold, 170-fold, 180-fold, 190-fold, 200-fold, or more than 200-fold increase in chlorogenic acid levels compared to chlorogenic acid levels from an equivalent product that is obtained from a non-transformed plant of the same species. In one embodiment, a plant or product has about a 3-fold increase in chlorogenic acid levels compared to chlorogenic acid levels from an equivalent product that is obtained from a non-transformed plant of the same species. In one embodiment, a plant or product has about a 4-fold increase in chlorogenic acid levels compared to chlorogenic acid levels from an equivalent product that is obtained from a non-transformed plant of the same species. In one embodiment, a plant or product has about a 5-fold increase in chlorogenic acid levels compared to chlorogenic acid levels from an equivalent product that is obtained from a non-transformed plant of the same species. In one embodiment, a plant or product has about a 6-fold increase in chlorogenic acid levels compared to chlorogenic acid levels from an equivalent product that is obtained from a non-transformed plant of the same species. In one embodiment, a plant or product has about a 7-fold increase in chlorogenic acid levels compared to chlorogenic acid levels from an equivalent product that is obtained from a non-transformed plant of the same species. In one embodiment, a plant or product has about a 8-fold increase in chlorogenic acid levels compared to chlorogenic acid levels from an equivalent product that is obtained from a non-transformed plant of the same species. In one embodiment, a plant or product has about a 9-fold increase in chlorogenic acid levels compared to chlorogenic acid levels from an equivalent product that is obtained from a non-transformed plant of the same species. In one embodiment, a plant or product has about a 10-fold increase in chlorogenic acid levels compared to chlorogenic acid levels from an equivalent product that is obtained from a non-transformed plant of the same species.

In one embodiment, a plant or product that is obtained from or made from any one of the plants transformed by any one of the present inventive methods, has at least about a 1-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 26-fold, 27-fold, 28-fold, 29-fold, 30-fold, 31-fold, 32-fold, 33-fold, 34-fold, 35-fold, 36-fold, 37-fold, 38-fold, 39-fold, 40-fold, 41-fold, 42-fold, 43-fold, 44-fold, 45-fold, 46-fold, 47-fold, 48-fold, 49-fold, 50-fold, 51-fold, 52-fold, 53-fold, 54-fold, 55-fold, 56-fold, 57-fold, 58-fold, 59-fold, 60-fold, 65-fold, 70-fold, 75-fold, 80-fold, 85-fold, 90-fold, 95-fold, 100-fold, 110-fold, 120-fold, 130-fold, 140-fold, 150-fold, 160-fold, 170-fold, 180-fold, 190-fold, 200-fold, or more than 200-fold increase in kaempferol levels compared to kaempferol levels from an equivalent product that is obtained from a non-transformed plant of the same species.

It is understood that a comparison of antioxidant levels of one or more antioxidants from a transformed plant or a product thereof is conducted against essentially the same amount of plant material of a control or non-transformed plant or product thereof. Accordingly, it is understood that, for instance, a "3-fold" increase in the level of an antioxidant means that equivalent amounts of transformed and non-transformed plant material is assayed for antioxidant levels. Furthermore, it is understood that the plant material being compared may be from transformed and non-transformed plants of the same species or variety.

In another embodiment of the present invention, the Cai gene or polynucleotide that is expressed according to the present inventive methods, encodes a protein that shares at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% sequence identity to the sequence of SEQ ID NO: 5.

In one embodiment, the antioxidant power of a plant or product thereof that is transformed according to the present invention is anywhere from about 100 µM Trolox equivalents (TE) gram$^{-1}$ to about 110 µM TE gram$^{-1}$, from about 100 µM TE gram$^{-1}$ to about 110 µM TE gram$^{-1}$, from about 100 µM TE gram$^{-1}$ to about 120 µM TE gram$^{-1}$, from about 100 µM TE gram$^{-1}$ to about 130 µM TE gram$^{-1}$, from about 100 µM TE gram$^{-1}$ to about 140 µM TE gram$^{-1}$, from about 100 µM TE gram$^{-1}$ to about 150 µM TE gram$^{-1}$, from about 100 µM TE gram$^{-1}$ to about 160 µM TE gram$^{-1}$, from about 100 µM TE gram$^{-1}$ to about 170 µM TE gram$^{-1}$, from about 100 µM TE gram$^{-1}$ to about 180 µM TE gram$^{-1}$, from about 100 µM TE gram$^{-1}$ to about 190 µM TE gram$^{-1}$, from about 100 µM TE gram$^{-1}$ to about 200 µM TE gram$^{-1}$, from about 100 µM TE gram$^{-1}$ to about 250 µM TE gram$^{-1}$, from about 100 µM TE gram$^{-1}$ to about 300 µM TE gram$^{-1}$, from about 100 µM TE gram$^{-1}$ to about 350 µM TE gram$^{-1}$, from about 100 µM TE gram$^{-1}$ to about 400 µM TE gram$^{-1}$, from about 100 µM TE gram$^{-1}$ to about 450 µM TE gram$^{-1}$, from about 100 µM TE gram$^{-1}$ to about 500 µM TE gram$^{-1}$, from about 100 µM TE gram$^{-1}$ to about 550 µM TE gram$^{-1}$, from about 100 µM TE gram$^{-1}$ to about 600 µM TE gram$^{-1}$, from about 100 µM TE gram$^{-1}$ to about 650 µM TE gram$^{-1}$, from about 100 µM TE gram$^{-1}$ to about 700 µM TE gram$^{-1}$, from about 100 µM TE gram$^{-1}$ to about 750 µM TE gram$^{-1}$, from about 100 µM TE gram$^{-1}$ to about 800 µM TE gram$^{-1}$, from about 100 µM TE gram$^{-1}$ to about 850 µM TE gram$^{-1}$, from about 100 µM TE gram$^{-1}$ to about 900 µM TE gram$^{-1}$, from about 100 µM TE gram$^{-1}$ to about 1000 µM TE gram$^{-1}$, or from about 100 µM TE gram$^{-1}$ to more than about 1000 µM TE gram$^{-1}$.

Another aspect of the present invention is a method for altering the level of an antioxidant in a potato plant or product thereof that produces a tuber with blue, red, or purple pigments, comprising expressing in the potato plant a nucleic acid that downregulates or inhibits the endogenous expression of at least one of (i) the F35h gene, (ii) the F3h gene, (iii) the Dfr gene, and (iv) the Chi gene, wherein the level of antioxidants in the plant expressing the nucleic acid is different to a blue- or purple pigmented potato plant of the same variety that does not express the nucleic acid. In one embodiment, the product of the plant is a potato or potato product, such as a chip, fry, crisp or other potato food.

In one embodiment, the potato plant that produces a tuber with blue, red, or purple pigments is selected from the group consisting of AC Blue Pride, AC Domino, Adirondack Blue, All Blue, Bleue d'Auvergne, Blue Mac, Brigus, British Columbia Blue, Caribe, Congo, Cowhorn, Glacier Blue, La Crotte d'Ours, Mayan Gold, Michigan Purple, OAC Royal Gold, Purple Peruvian, Purple Viking, Ruby Pulsiver's Blue Noser, True Blue, and Vitelette.

In another embodiment, the potato obtained from the potato plant produces a tuber with blue, red, or purple pigments that expresses the nucleic acid has increased levels of at least one of kaempferol and chalcone antioxidants.

Another aspect of the present invention is a blue, red, or purple pigmented potato that comprises in its genome a nucleic acid that downregulates or inhibits the endogenous expression of at least one of (i) the F35h gene, (ii) the F3h gene, (iii) the Dfr gene, and (iv) the Chi gene.

Another aspect of the present invention is a method for reducing the level of glycoalkaloids in a tuber, comprising overexpressing the Cai gene or a polynucleotide that encodes a protein that shares at least 90% sequence identity with the protein encoded by the Cai gene in the skin cells or at least one tissue of a tuber, wherein the level of glycoalkaloid in the skin of that tuber is lower than the level of glycoalkaloid in the skin of a tuber that does not overexpress the Cai gene or polynucleotide.

Another aspect of the present invention is a tuber, comprising a nucleic acid construct that expresses the Cai gene in skin cells or at least one tissue of the tuber. In one embodiment, the Cai gene that is expressed in the tuber skin encodes a protein that shares at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% sequence identity to the sequence of SEQ ID NO: 5.

A tuber of the present invention may be, but is not limited to, a beet, carrot, cassava, chicory roots, garlic, ginger, onion, potato, sweet potato, taro, parsnip, dasheen, malanga, jicama, lotus root, Jerusalem artichoke, rutabaga, or a yam.

A potato of the present invention is grown from a transformed potato plant of the present invention and may be, but is not limited to, those that are grown from a potato plant that produces a potato commonly known as a baby potato, a baking potato, a Bintje potato, a blue potato, a boiling potato, a Caribe potato, a chat potato, a russet potato, a fingerling potato, a Finnish yellow wax potato, a huckleberry potato, an Idaho potato, a long white potato, a low-starch potato, purple Peruvian potato, red-skinned potato, starchy potato, waxy potato, white round potato, Yellow Finn potato, Yukon Gold potato, or any wild potato species, such as *Solanum phureja*.

One aspect of the present invention is a method for increasing the level of antioxidants known as anthocyanins and chlorogenic acid in a plant tissue comprising overexpressing a gene encoding a protein that shares at least 90% identity with the mCai protein shown in SEQ ID NO. 5. In one embodiment, an untransformed plant of the same species or variety does not normally constitutively produce anthocyanins, Another aspect of the present invention is a method for increasing the level of kaempferol and chlorogenic acid in a plant tissue that does not constantly produce anthocyanins, comprising (i) overexpressing a gene encoding a protein that shares at least 90% identity with the mCai protein shown in SEQ ID NO. 5, and (ii) expressing a polynucleotide that inhibits or downregulates the expression of the F35h gene in the plant, wherein the accumulation of anthocyanins is reduced compared to that of a plant that overexpresses the Cai gene but is not downregulated in F35h gene expression. In one embodiment, the polynucleotide comprises the nucleotide sequence of SEQ ID NO. 10 or SEQ ID NO. 11.

Another aspect increases the levels of kaempferol and chlorogenic acid in a plant tissue, comprising (i) overexpressing a gene encoding a protein that shares at least 90% identity with the mCai protein shown in SEQ ID NO. 5, and (ii) expressing a polynucleotide that inhibits or downregulates the expression of the F3h gene in the plant, wherein the accumulation of anthocyanins is reduced compared to that of a plant that overexpresses the Cai gene but is not downregulated in F3h gene expression. In one embodiment, an untransformed plant of the same species or variety does not normally constitutively produce anthocyanins, Another aspect increases the levels of flavonols and chlorogenic acid in a plant tissue, comprising (i) overexpressing a gene encoding a protein that shares at least 90% identity with the mCai protein shown in SEQ ID NO. 5, and (ii) expressing a polynucleotide that inhibits or downregulates the expression of the Dfr gene in the plant, wherein the accumulation of anthocyanins is reduced compared to that of a plant that overexpresses the Cai gene but is not downregulated in Dfr gene expression. In one embodiment, the polynucleotide comprises the nucleotide sequence of SEQ ID NO. 12. In one embodiment, an untransformed plant of the same species or variety does not normally constitutively produce anthocyanins, Another aspect increases the levels of chalcone and chlorogenic acid in a plant tissue, comprising (i) overexpressing a gene encoding a protein that shares at least 90% identity with the mCai protein shown in SEQ ID NO. 5, and (ii) expressing a polynucleotide that inhibits or downregulates the expression of the Chi gene in the plant, wherein the accumulation of anthocyanins is reduced compared to that of a plant that overexpresses the Cai gene but is not downregulated in Chi gene expression. In one embodiment, an untransformed plant of the same species or variety does not normally constitutively produce anthocyanins, One aspect of the present invention is a method for increasing the level of specific phenolic compounds in a plant tissue that produces delphindins, comprising expressing a polynucleotide that inhibits or downregulates the expression of the F35h gene in the plant, wherein the accumulation of delphindins is reduced compared to that of a plant that is not downregulated in F35h gene expression.

Another aspect increases the levels of specific phenolic compounds in a plant tissue that produces cyanidins, comprising expressing a polynucleotide that inhibits or downregulates the expression of the F3h gene in the plant, wherein the accumulation of cyanidins is reduced compared to that of a plant that is not downregulated in F3h gene expression.

Another aspect increases the levels of specific phenolic compounds in a plant tissue that produces anthocyanins, comprising expressing a polynucleotide that inhibits or downregulates the expression of the Dfr gene in the plant, wherein the accumulation of anthocyanins is reduced compared to that of a plant that is not downregulated in Dfr gene expression.

Another aspect increases the levels of chalcone and chlorogenic acid in a plant tissue that produces anthocyanins, comprising expressing a polynucleotide that inhibits or downregulates the expression of the Chi gene in the plant, wherein the accumulation of anthocyanins is reduced compared to that of a plant that is not downregulated in Chi gene expression.

In one embodiment of any method of the present invention, a desired polynucleotide may comprise a Cai gene, or a derivative thereof, operably linked to an upstream (5') promoter and downstream (3') terminator. A desired polynucleotide may be positioned within the borders of a transfer DNA, such as a T-DNA or P-DNA, and may either comprise the Cai gene expression cassette as single expression cassette or together with at least one additional expression cassette. A desired polynucleotide may be mutated or a variant of its wild-type sequence. It is understood that all or part of the desired polynucleotide can be integrated into the genome of a plant. In another embodiment, a desired polynucleotide of the present invention may comprise any expression cassette and express any gene and is therefore not limited to expressing a Cai gene only. For instance, instead of the Cai gene, it is possible to use other genes that activate anthocyanin biosynthesis such as tomato Ant1, *Arabidopsis* Pap1, and the maize Lc/C1 system.

In one embodiment, the protein is produced by an expression cassette comprising, from 5' to 3', a promoter, a polynucleotide encoding the protein, and a terminator.

In another embodiment, the promoter is a tissue-specific promoter selected from the group consisting of a potato granule bound starch synthase gene promoter, a potato ADP-glucose pyrophosphorylase gene promoter, a potato patatin promoter, a potato flavanoid 3-monooxygenase gene promoter, a tomato 2A11 promoter, a tomato E8 promoter, an alfalfa Pal2 promoter, or an *Arabidopsis* AtPUP1 promoter.

Particularly, the granule bound starch synthase gene promoter may comprise at least part of the sequence of SEQ ID NO. 6; the ADP-glucose pyrophosphorylase gene promoter may comprise at least part of the sequence of SEQ ID NO. 7; the 2A11 promoter may comprise at least part of SEQ ID NO. 13, and the E8 promoter may comprise at least part of SEQ ID NO. 14.

In another embodiment, the promoter is a pathogen-inducible promoter selected from the group consisting of an Asparagus AoPR1 promoter, a tobacco or *Arabidopsis* PR1 promoter, a potato Wun1 or Win1 promoter, a maize ZmPR4 promoter, a poplar win3.12T promoter, or a pine PR10 promoter.

In a further embodiment, the increased levels of an antioxidant phenolic are in a tuber or fruit of the plant.

In one embodiment of any of the methods or compositions of the present invention, the plant is a potato plant, tomato plant, pepper plant, cassava plant, or an eggplant.

Another aspect of the present invention is an isolated polynucleotide sequence comprising (a) the sequence of SEQ ID NO: 3 or (b) a Myb transcription factor gene, which is engineered to encode a protein that contains a threonine residue at position 4 and a serine residue at position 5.

In another aspect of the present invention is a method for increasing an antioxidant level in a plant, comprising overexpressing the polynucleotide of claim 12 in a plant, wherein overexpression of the polynucleotide is associated with an increased antioxidant level in the plant compared to the level of antioxidant in a plant that overexpresses a Myb transcription factor gene, that does not contain a threonine residue at position 4 and a serine residue at position 5.

Another aspect of the present invention is a method of identifying a transformed plant comprising the following steps; (i) transformation of an explant of a Solanaceous plant species with a transfer DNA comprising a Cai gene operably linked to a functional promoter; (ii) identification of a regenerated shoot that displays a purple pigmentation, (iii) rooting of the shoot, and transfer to soil.

One other aspect of the present invention is a tuber or a fruit, comprising in its genome a sequence that displays at least 90% identity with the sequence depicted in SEQ ID NO. 3. In one embodiment, the tuber has increased levels of chlorogenic acid compared to a tuber with a genome that does not comprise the sequence depicted in SEQ ID NO. 5.

In another embodiment, the tuber of a genetically modified plant contains at least a three-fold higher level of chlorogenic acid than the tuber of an untransformed, but otherwise genetically identical, plant.

In another embodiment, the tuber of a genetically modified plant contains at least a ten-fold higher level of flavonols than the tuber of an untransformed, but otherwise genetically identical, plant.

In one embodiment, the tuber of a genetically modified plant contains at least a two-fold lower level of glycoalkaloids than the tuber of an untransformed but otherwise genetically identical plant.

Another aspect of the present invention is a plant cell that contains a gene encoding a protein that shares at least about 85% or at least about 90% sequence identity with the mCai protein shown in SEQ ID NO. 5, wherein (i) the gene is linked to a promoter that is different from its original promoter and (ii) gene expression levels are higher than in the plant cell that contains the gene linked to its original promoter. In one embodiment, the plant cell is in a plant, which subsequently has at least one altered trait compared to a plant that does not contain the plant cell which overexpresses the mCai protein. In one embodiment, the altered plant trait is at least one of (i) an increased level of chlorogenic acid, (ii) an increased level of an anthocyanin, (iii) an increased level of a flavonol, (iv) a reduced level of a glycoalkaloid, or (v) an increased level of another phenolic compound that displays antioxidant activities.

Another aspect of the present invention is a method for accelerating the suberization of wounded plant tissue by overexpressing the Cai gene or a modified Cai gene, such as mCai, in the plant. In one embodiment, the Cai gene or modified Cai gene is expressed throughout all of the plant's tissues. In another embodiment, expression of the Cai gene or the modified Cai gene results in increased levels of phenolic compounds in the plant. In another embodiment, the increased levels of phenolic compounds are in the periderm tissue of a potato of a potato plant that expresses the Cai gene or the modified Cai gene.

Another aspect of the present invention is a method for enhancing a plant's tolerance against bacterial pathogens. In one embodiment, the method comprises overexpressing the Cai gene in a plant, such as in potato, sweet pepper, hot pepper, or eggplant. In one embodiment, the overexpressed Cai gene increases chlorogenic acid levels, which in turn enhances the tolerance of the plant against various pathogens, such as, in the case of potato: *Pseudomonas syringae*, *Erwinia carotovora*, (causal agent of tuber soft rot), *Streptomyces scabies*, (causes common scab).

In another embodiment, a transgenic tomato plant, which overexpresses the Cai gene will display enhanced tolerance against bacterial pathogens including *Xanthomonas vesicatoria*, which causal bacterial spot, and the bacterial speck-causing *Pseudomonas syringae*.

In another embodiment, Cai gene overexpression can trigger partial tolerance against fungal pathogens such as *Cercospora nicotianae* and *Fusarium oxysporum*.

BRIEF DESCRIPTION OF THE DRAWINGS

FIG. 1: Alignment depicting amino acid sequence homology among Myb transcription factors having the protein sequences SEQ ID NOs 17-27. Homology among Myb transcription factors. StCai=Cai gene from potato (SEQ ID NO. 1; cDNA is SEQ ID NO. 2); LeANT1=Ant1 gene from tomato (SEQ ID NO. 17); StAN2=An2 gene from potato (SEQ ID NO. 18); StANT1=Ant1 gene from potato (SEQ ID NO. 19); CaA=A gene from pepper (SEQ ID NO. 20); PhAN2=An2 gene from *Petunia hybrida* (SEQ ID NO. 21); V1MYBA1=MybA1 gene from Kyoho grape (SEQ ID NO. 22); IpMYP1=Myb1 gene from common morning-glory (SEQ ID NO. 23); AmVENOSA=VENOSA gene from snapdragon (SEQ ID NO. 24); AtPAP1=Pap1 gene from Arabidospsis (SEQ ID NO. 25); ZmC1=C1 gene from maize (SEQ ID NO. 26); AtTT2=Tt2 gene from *Arabidopsis* (SEQ ID NO. 27).

FIG. 2: Schematic representations of binary vector transfer DNAs used in the present invention to facilitate the overexpression of polynucleotides that increase the amount of phenolic compounds with antioxidant activity.

DETAILED DESCRIPTION OF THE PREFERRED EMBODIMENTS

Figure 3:
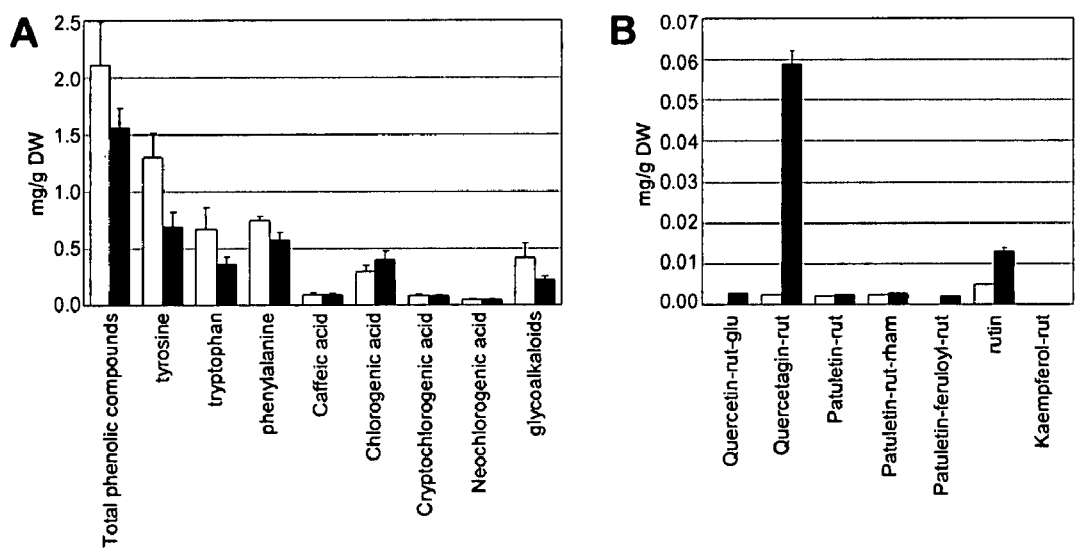
FIG. 3. HPLC analysis of Bintje tubers from a transgenic control (light bars) and line 646-14 (dark bars). Rut=rutinose; rham=rhamnose; glu=glucoside.

The present invention provides polynucleotide sequences and methods for increasing the amount of phenolic compounds with antioxidant activity, such as chlorogenic acid, kaempferol, caffeoyl putrescine, and various flavonols, in a plant or product thereof. The methods employed herein also may be adapted to decrease the levels of antinutritional glycoalkaloids.

The phenylpropanoid (PP) pathway utilizes phenylalanine as a substrate for the production of a broad variety of phenolic compounds. Activation of this pathway may reduce the accumulation of certain phenylalanine-related compounds such as the aromatic amino acids tyrosine and tryptophan, as well as reduce the concentration of phenylalanine itself, without negatively affecting plant development. More importantly, this modification can also increase the levels of phenolic compounds that display antioxidant properties, whereas the concentrations of undesirable compounds such as glycoalkaloids may be reduced.

Three of the groups of compounds that are produced by the PP pathway are: (i) lignins, (ii) flavonoids, and (iii) caffeoyl-containing phenolic compounds, such as chlorogenic acid.

Enzymes involved in the biosynthesis of the first group of compounds include phenylalanine ammonium lyase (Pal), cinnamate-4-hydroxylase (C4H), and 4:coumarate:CoA ligase (4CL). Intermediary compounds of this pathway include caffeic acid, ferulic-coA, 5-hydroxy ferulic-coA, and sinapic acid. Various transcription factors are known to regulate parts of the phenylpropanoid pathway. Examples of transcription factors involved in lignin biosynthesis, for example, include Eucalyptus EgMYB2 and tobacco NtLim1.

The second group of phenolics includes flavones, flavonols, anthocyanins, and tannins. The production of these compounds requires the activity of enzymes such as chalcone synthase (Chs) and chalcone isomerase (Chi), which catalyze the conversion of p-coumaroyl-coA, through tetrahydroxychalcone, into naringenin. Naringenin is then converted into either flavones or flavonols, such as quercetin and kaempferol, by enzymes that include flavone synthase (FS), flavanone-3-beta-hydroxylase (F3H), flavonoid 3'-hydroxylase (F3'H), and flavonoid 3'-5' hydroxylase (F3'5'H). Biosynthesis of anthocyanins such as pelargonidin, cyaniding, and delphinidin often requires a functional dihydroflavonol 4-reductase (Dfr).

Transcription factors involved in the production of anthocyanins can be divided into four groups of proteins: (i) Myb transcription factors such as C1, P1, and P of maize, An2 and An4 of *Petunia hybrida*, AmMYB305 and AmMYB340 of snapdragon, Tt2 and Pap1 of *Arabidopsis*, and Ant1 of tomato, (ii) Myc transcription factors including R and B of maize, An1 and Jaf13 of *P. hybrida*, Snapdragon Delila, and *Arabidopsis* Tt8, (iii) the WD40 factors An11 of *P. hybrida* and ttg1 of *Arabidopsis*, and (iv) the *Arabidopsis* WKRY transcription factors Ttg2, Tt1, and An12.

The third group of phenolic compounds consists of caffeoyl-containing compounds such as caffeoyl putrescine and chlorogenic acid. Hydroxycinnamoyl transferase (Hqt) has been proposed to mediate the conversion of quinic acid and caffeic acid into chlorogenic acid (Niggeweg et al., Nat Biotechnol 22: 746-754). However, overexpression of the Hqt gene only results in an about 1.5-fold increase in the levels of chlorogenic acid, which makes it unlikely that this gene plays the key regulatory role in the biosynthesis of caffeoyl-containing compounds.

The present invention provides a newly-isolated and identified gene from potato, the chlorogenic acid-inducing (Cai) gene, which shares some sequence homology with various Myb transcription factors (FIG. 1). The predicted Cai protein sequence displays 85.3% identity with tomato Ant1 protein, and 61.3% identity with potato An2.

Surprisingly, as explained in detail below, and in the Examples, the results of the present inventive methods, which entail overexpression of the Cai gene in certain tissues such as the flesh of potato tubers, show an increased accumulation of chlorogenic acid and related caffeoyl-containing compounds including crypto-chlorogenic acid, neo-chlorogenic acid, and caffeoyl putrescine. Furthermore, Cai gene overexpression in the tuber skin results in the reduced accumulation of the antinutritional glycoalkaloids chaconine and solanine.

The improvements in the nutritional characteristics of a food crop that can be accomplished through overexpression of the Cai gene are particularly effective if applied to the edible parts of Solanaceous crops such as potato tubers and the fruits of tomato, sweet pepper, and eggplant.

These improvements can be accomplished by operably linking either the Cai gene or a derivative thereof to specific promoters. Such promoters induce either near-constitutive Cai gene expression or overexpression of the Cai gene predominantly or exclusively in tubers or fruits.

Thus, overexpression of the Cai protein in the flesh of potato tubers can induce the expression of at least one of the genes involved in the biosynthesis of certain caffeoyl-containing compounds such as chlorogenic acid and related phenolics, which, in turn, results in a potato tuber with increased levels of beneficial antioxidant activity.

The present invention uses terms and phrases that are well known to those in the art of molecular biology and plant physiology. Unless defined otherwise, all technical and scientific terms used herein have the same meaning as commonly understood by one of ordinary skill in the art to which this invention belongs. Generally, the nomenclature used herein, and the laboratory procedures in cell culture, molecular genetics, and nucleic acid chemistry and hybridization described herein are those well known and commonly employed in the art. Standard techniques are used for recombinant nucleic acid methods, polynucleotide synthesis, microbial culture, cell culture, tissue culture, transformation, transfection, transduction, analytical chemistry, organic synthetic chemistry, chemical syntheses, chemical analysis, and pharmaceutical formulation and delivery. Generally, enzymatic reactions and purification and/or isolation steps are performed according to the manufacturers' specifications. The techniques and procedures are generally performed according to conventional methodology (Molecular Cloning, A Laboratory Manual, 3rd. edition, edited by Sambrook & Russel Cold Spring Harbor Laboratory Press, Cold Spring Harbor, N.Y., 2001).

Bacterium-mediated transformation: as is well known in the field, Agrobacteria that are used for transforming plant cells are disarmed and virulent derivatives of *Agrobacterium tumefaciens* and *Agrobacterium rhizogenes*. These bacteria contain a plasmid that carries a desired polynucleotide positioned between border sequences. Such border sequences can be derived from either *Agrobacterium* Ti plasmids or plant DNA (Rommens et al, Plant Physiol 139: 1338-1349), and can also be designed synthetically (Rommens et al, Plant Physiol 139: 1338-1349). As an alternative to using Agrobacteria, it is also possible to employ bacteria such as *Rhizobium trifolii, Rhizobium leguminosarum, Phyllobacterium myrsinacearum, SinoRhizobium meliloti*, and *MesoRhizobium loti*.

Angiosperm: vascular plants having seeds enclosed in an ovary. Angiosperms are seed plants that produce flowers that bear fruits. Angiosperms are divided into dicotyledonous and monocotyledonous plants.

Antibiotic Resistance: ability of a cell to survive in the presence of an antibiotic. Antibiotic resistance, as used herein, results from the expression of an antibiotic resistance gene in a host cell. A cell may have antibiotic resistance to any antibiotic.

Cai gene: this potato gene, shown in SEQ ID NO.: 1 encodes a Myb transcription factor. Overexpression of a modified Cai gene that encodes for a protein with a threonine and serine residue at positions 4 and 5, respectively, in the flesh of potato tubers induces the expression of at least one gene involved in the biosynthesis of chlorogenic acid. The alternative overexpression in tuber skins leads to an about two-fold reduction in glycoalkaloid level. A Cai gene of the present invention may express a protein that shares at least 80%, or at least 85% or at least 90%, or at least 95% sequence identity with the amino acid sequence of SEQ ID NO: 5.

Dicotyledonous plant (dicot): a flowering plant whose embryos have two seed halves or cotyledons, branching leaf veins, and flower parts in multiples of four or five. Examples of dicots include, but are not limited to, potato, sugar beet, broccoli, cassava, sweet potato, pepper, poinsettia, bean, alfalfa, soybean, and avocado.

Endogenous: nucleic acid, gene, polynucleotide, DNA, RNA, mRNA, or cDNA molecule that is isolated either from the genome of a plant or plant species that is to be transformed or is isolated from a plant or species that is sexually compatible or interfertile with the plant species that is to be transformed, is "native" to, i.e., indigenous to, the plant species.

Foreign: "foreign," with respect to a nucleic acid, means that that nucleic acid is derived from non-plant organisms, or derived from a plant that is not the same species as the plant to be transformed, or is derived from a plant that is not interfertile with the plant to be transformed. According to the present invention, foreign DNA or RNA represents nucleic acids that are naturally occurring in the genetic makeup of fungi, bacteria, viruses, mammals, fish or birds, but are not naturally occurring in the plant that is to be transformed. Thus, a foreign nucleic acid is one that encodes, for instance, a polypeptide that is not naturally produced by the transformed plant. A foreign nucleic acid does not necessarily encode a protein product, but may produce an undesirable or desirable RNA product.

Gene: A gene is a segment of a DNA molecule that contains all the information required for synthesis of a product, polypeptide chain or RNA molecule that may include both coding and non-coding sequences.

Genetic element: a "genetic element" is any discreet nucleotide sequence that displays a specific function such as, but not limited to, a promoter, gene, terminator, intron, enhancer, spacer, 5'-untranslated region, 3'-untranslated region, or transfer DNA border.

Genetic modification: stable introduction of a specific DNA segment into the genome of a plant by applying methods in molecular and cell biology.

Gymnosperm: as used herein, refers to a seed plant that bears seed without ovaries. Examples of gymnosperms include conifers, cycads, ginkgos, and ephedras.

Introduction: as used herein, refers to the insertion of a nucleic acid sequence into a cell, by methods including, but not limited to, infection, transfection, transformation or transduction.

Monocotyledonous plant (monocot): a flowering plant having embryos with one cotyledon or seed leaf, parallel leaf veins, and flower parts in multiples of three. Examples of monocots include, but are not limited to maize, rice, oat, wheat, barley, and sorghum.

Native: a nucleic acid, gene, polynucleotide, DNA, RNA, mRNA, or cDNA molecule that is isolated either from the genome of a plant or plant species that is to be transformed, or is isolated from a plant or species that is sexually compatible or interfertile with the plant species that is to be transformed, is "native" to, i.e., indigenous to, the plant species. A native polynucleotide sequence is indigenous to the transformed plant species. A native polynucleotide can include modifications to the nucleic acid sequence isolated from the plant or plant species to be transformed, including base-pair substitutions, rearrangements, deletions, and insertions, among others made in vitro or in vivo by methods well-known to the skilled artisan such as those based on the polymerase chain reaction.

Native DNA: any nucleic acid, gene, polynucleotide, DNA, RNA, mRNA, or cDNA molecule that is isolated either from the genome of a plant or plant species that is to be transformed or is isolated from a plant or species that is sexually compatible or interfertile with the plant species that is to be transformed. A native polynucleotide is indigenous to the plant species to be transformed. In other words, a native genetic element represents all genetic material that is accessible to plant breeders for the improvement of plants through classical plant breeding. Any variants of a native nucleic acid also are considered "native" in accordance with the present invention. For instance, a native DNA may comprise a point mutation since such point mutations occur naturally. It is also possible to link two different native DNAs by employing restriction sites because such sites are ubiquitous in plant genomes.

Operably linked: combining two or more molecules in such a fashion that in combination they function properly in a plant cell. For instance, a promoter is operably linked to a structural gene when the promoter controls transcription of the structural gene.

P-DNA: a plant-derived transfer-DNA ("P-DNA") border sequence of the present invention is not identical in nucleotide sequence to any known bacterium-derived T-DNA border sequence, but it functions for essentially the same purpose. That is, the P-DNA can be used to transfer and integrate one polynucleotide into another. A P-DNA can be inserted into a tumor-inducing plasmid, such as a Ti-plasmid from *Agrobacterum* in place of a conventional T-DNA, and maintained in a bacterium strain, just like conventional transformation plasmids. The P-DNA can be manipulated so as to contain a desired polynucleotide, which is destined for integration into a plant genome via bacteria-mediated plant transformation. See Rommens et al. in WO2003/069980, US-2003-0221213, US-2004-0107455, and WO2005/004585, which are all incorporated herein by reference. The use of P-DNA may result in a plant or plant cell transformed with all-native DNA.

Phenotype: phenotype is a distinguishing feature or characteristic of a plant, which may be altered according to the present invention by integrating one or more "desired polynucleotides" and/or screenable/selectable markers into the genome of at least one plant cell of a transformed plant. The "desired polynucleotide(s)" and/or markers may confer a change in the phenotype of a transformed plant, by modifying any one of a number of genetic, molecular, biochemical, physiological, morphological, or agronomic characteristics or properties of the transformed plant cell or plant as a whole. Thus, expression of one or more, stably integrated desired polynucleotide(s) in a plant genome that results in increased concentration of a phenolic compound such as chlorogenic acid in a plant cell, plant organ, or plant, such as a tuber or fruit, is an example of a phenotype modified by the present invention.

Plant tissue: a "plant" is any of various photosynthetic, eukaryotic, multicellular organisms of the kingdom Plantae characteristically producing embryos, containing chloroplasts, and having cellulose cell walls. A part of a plant, i.e., a "plant tissue" may be treated according to the methods of the present invention to produce a transgenic plant. Many suitable plant tissues can be transformed according to the present invention and include, but are not limited to, somatic embryos, pollen, leaves, stems, calli, stolons, microtubers, and shoots. Thus, the present invention envisions the transformation of angiosperm plants such as wheat, maize, rice, barley, oat, sugar beet, potato, tomato, alfalfa, cassava, sweet potato, and soybean to produce a plant cell, plant tissue, plant organ, plant-derived product, or plant with an increased level of at least one phenolic compound such as chlorogenic acid. According to the present invention "plant tissue" also encompasses plant cells. Plant cells include suspension cultures, callus, embryos, meristematic regions, callus tissue, leaves, roots, shoots, gametophytes, sporophytes, pollen, seeds and microspores. Plant tissues may be at various stages of maturity and may be grown in liquid or solid culture, or in soil or suitable media in pots, greenhouses or fields. A plant tissue also refers to any clone of such a plant, seed, progeny, propagule whether generated sexually or asexually, and descendents of any of these, such as cuttings or seed. Of particular interest are potato, maize, and wheat.

Plant transformation and cell culture: broadly refers to the process by which plant cells are genetically modified and transferred to an appropriate plant culture medium for maintenance, further growth, and/or further development into plants. Such methods are well known to the skilled artisan.

Progeny: a "progeny" of the present invention, such as the progeny of a transgenic plant, is one that is born of, begotten by, or derived from a plant or the transgenic plant. Thus, a "progeny" plant, i.e., an "F1" generation plant is an offspring or a descendant of the transgenic plant produced by the inventive methods. A progeny of a transgenic plant may contain in at least one, some, or all of its cell genomes, the desired polynucleotide that was integrated into a cell of the parent transgenic plant by the methods described herein. Thus, the desired polynucleotide is "transmitted" or "inherited" by the progeny plant. The desired polynucleotide that is so inherited in the progeny plant may reside within a T-DNA or P-DNA construct, which also is inherited by the progeny plant from its parent. The term "progeny" as used herein, also may be considered to be the offspring or descendants of a group of plants.

Promoter: a promoter is intended to mean a nucleic acid, preferably DNA that binds RNA polymerase and/or other transcription regulatory elements. As with any promoter, the promoters of the current invention will facilitate or control the transcription of DNA or RNA to generate an mRNA molecule from a nucleic acid molecule that is operably linked to the promoter. As stated earlier, the RNA generated may code for a protein or polypeptide or may code for an RNA interfering, or antisense molecule.

A plant promoter is a promoter capable of initiating transcription in plant cells whether or not its origin is a plant cell. Exemplary plant promoters include, but are not limited to, those that are obtained from plants, plant viruses, and bacteria such as *Agrobacterium* or *Rhizobium* which comprise genes expressed in plant cells. Examples of promoters under developmental control include promoters that preferentially initiate transcription in certain tissues, such as xylem, leaves, roots, or seeds. Such promoters are referred to as tissue-preferred promoters. Promoters which initiate transcription only in certain tissues are referred to as tissue-specific promoters. A cell type-specific promoter primarily drives expression in certain cell types in one or more organs, for example, vascular cells in roots or leaves. An inducible or repressible promoter is a promoter which is under environmental control. Examples of environmental conditions that may effect transcription by inducible promoters include anaerobic conditions or the presence of light. Tissue specific, tissue preferred, cell type specific, and inducible promoters constitute the class of non-constitutive promoters. A constitutive promoter is a promoter which is active under most environmental conditions, and in most plant parts.

Polynucleotide: is a nucleotide sequence, comprising a gene coding sequence or a fragment thereof, (comprising at least 15 consecutive nucleotides, preferably at least 30 consecutive nucleotides, and more preferably at least 50 consecutive nucleotides), a promoter, an intron, an enhancer region, a terminator comprising the 3'-end mRNA processing signals, a translation initiation site, 5' or 3' untranslated regions, a reporter gene, a selectable marker or the like. The polynucleotide may comprise genomic DNA, an RNA transcript (such as an mRNA) or a processed nucleotide sequence (such as a cDNA). The polynucleotide may comprise a sequence in either sense or antisense orientations.

An isolated polynucleotide is a polynucleotide separated from nucleotide sequences with which it typically is in proximity, or is next to nucleotide sequences with which it typically is not in proximity.

Seed: a "seed" may be regarded as a ripened plant ovule containing an embryo, and a propagative part of a plant, as a tuber or spore. Seed may be incubated prior to *Agrobacterium*-mediated transformation, in the dark, for instance, to facilitate germination. Seed also may be sterilized prior to incubation, such as by brief treatment with bleach. The resultant seedling can then be exposed to a desired strain of *Agrobacterium*.

Selectable/screenable marker: a gene that, if expressed in plants or plant tissues, makes it possible to distinguish them from other plants or plant tissues that do not express that gene. Screening procedures may require assays for expression of proteins encoded by the screenable marker gene. Examples of selectable markers include the neomycin phosphotransferase (nptII) gene encoding kanamycin and geneticin resistance, the hygromycin phosphotransferase (hptII) gene encoding resistance to hygromycin, or other similar genes known in the art. Examples of a screenable marker include the green florescent protein gene or the gas gene, among others.

Sequence identity: as used herein, "sequence identity" or "identity" in the context of two nucleic acid or polypeptide sequences includes reference to the residues in the two sequences which are the same when aligned for maximum correspondence over a specified region. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non conservative substitution is given a score of zero, a conservative substitution is given a score between zero and 1. The scoring of conservative substitutions is calculated, e.g., according to the algorithm of Meyers and Miller, Computer Applic. Biol. Sci., 4: 11 17 (1988) e.g., as implemented in the program PC/GENE (Intelligenetics, Mountain View, Calif., USA).

As used herein, percentage of sequence identity means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

"Sequence identity" has an art-recognized meaning and can be calculated using published techniques. See COMPUTATIONAL MOLECULAR BIOLOGY, Lesk, ed. (Oxford University Press, 1988), BIOCOMPUTING: INFORMATICS AND GENOME PROJECTS, Smith, ed. (Academic Press, 1993), COMPUTER ANALYSIS OF SEQUENCE DATA, PART I, Griffin & Griffin, eds., (Humana Press, 1994), SEQUENCE ANALYSIS IN MOLECULAR BIOLOGY, Von Heinje ed., Academic Press (1987), SEQUENCE ANALYSIS PRIMER, Gribskov & Devereux, eds. (Macmillan Stockton Press, 1991), and Carillo & Lipton, SIAM J. Applied Math. 48: 1073 (1988). Methods commonly employed to determine identity or similarity between two sequences include, but are not limited to, those disclosed in GUIDE TO HUGE COMPUTERS, Bishop, ed., (Academic Press, 1994) and Carillo & Lipton, supra. Methods to determine identity and similarity are codified in computer programs. Preferred computer program methods to determine identity and similarity between two sequences include, but are not limited to, the GCG program package (Devereux et al., Nucleic Acids Research 12: 387 (1984)), BLASTP, BLASTN, FASTA (Atschul et al., J. Mol. Biol. 215: 403 (1990)), and FASTDB (Brutlag et al., Comp. App. Biosci. 6: 237 (1990)).

Transcriptional terminators: The expression DNA constructs of the present invention typically have a transcriptional termination region at the opposite end from the transcription initiation regulatory region. The transcriptional termination region may be selected, for stability of the mRNA to enhance expression and/or for the addition of polyadenylation tails added to the gene transcription product. Translation of a nascent polypeptide undergoes termination when any of the three chain-termination codons enters the A site on the ribosome. Translation termination codons are UAA, UAG, and UGA.

In the instant invention, transcription terminators are derived from (i) both an approximately 100 to 300-basepair DNA region comprising the untranslated 3' sequences of a gene and 100 to 300-basepair sequences immediately downstream from this so-called trailer, or (ii) intergenic DNA that displays inadvertent terminator-like activity. For example, the terminator from the potato ubiquitin gene, may be used.

Transfer DNA (T-DNA): an *Agrobacterium* T-DNA is a genetic element that is well-known as an element capable of integrating a nucleotide sequence contained within its borders into another genome. In this respect, a T-DNA is flanked, typically, by two "border" sequences. A desired polynucleotide of the present invention and a selectable marker may be positioned between the left border-like sequence and the right border-like sequence of a T-DNA. The desired polynucleotide and selectable marker contained within the T-DNA may be operably linked to a variety of different, plant-specific (i.e., native), or foreign nucleic acids, like promoter and terminator regulatory elements that facilitate its expression, i.e., transcription and/or translation of the DNA sequence encoded by the desired polynucleotide or selectable marker.

Transformation of plant cells: A process by which a nucleic acid is stably inserted into the genome of a plant cell. Transformation may occur under natural or artificial conditions using various methods well known in the art. Transformation may rely on any known method for the insertion of nucleic acid sequences into a prokaryotic or eukaryotic host cell, including *Agrobacterium*-mediated transformation protocols such as "refined transformation" or "precise breeding." See U.S. application publication Nos. 20030221213, 20040107455, 20040003434, and 20050034188, which are all incorporated herein by reference. Transformation may rely on other known methods for the insertion of nucleic acid sequences into a prokaryotic or eukaryotic host cell, including viral infection, whiskers, electroporation, microinjection, polyethylene glycol-treatment, heat shock, lipofection and particle bombardment.

Transgenic plant: a transgenic plant of the present invention is one that comprises at least one cell genome in which an exogenous nucleic acid has been stably integrated. According to the present invention, a transgenic plant is a plant that comprises only one genetically modified cell and cell genome, or is a plant that comprises some genetically modified cells, or is a plant in which all of the cells are genetically modified. A transgenic plant of the present invention may be one that comprises expression of the desired polynucleotide, i.e., the exogenous nucleic acid, in only certain parts of the plant. A transgenic plant of the present invention, may, or may not be, capable of transmitting the integrated transfer DNA to progeny through sexual reproduction. It may also be capable of transmitting the transfer DNA to clones obtained by either propagation of planting tubers or tuber pieces.

Variant: a "variant," as used herein, is understood to mean a nucleotide or amino acid sequence that deviates from the standard, or given, nucleotide or amino acid sequence of a particular gene or protein. The terms, "isoform," "isotype," and "analog" also refer to "variant" forms of a nucleotide or an amino acid sequence. An amino acid sequence that is altered by the addition, removal or substitution of one or more amino acids, or a change in nucleotide sequence, may be considered a "variant" sequence. The variant may have "conservative" changes, wherein a substituted amino acid has similar structural or chemical properties, e.g., replacement of leucine with isoleucine. A variant may have "nonconservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art such as Vector NTI Suite (InforMax, MD) software. "Variant" may also refer to a "shuffled gene" such as those described in Maxygen-assigned patents.

Promoters

A promoter is a genetic regulatory element that mediates the transcription of a downstream DNA sequence. Transcription is initiated at the transcription start site, which functions as binding site for RNA polymerase II. The transcription start is often positioned about xx-base pairs downstream from a TATA-box, the binding site for a large complex of some 50 different proteins, including (i) Transcription Factor IID (TFIID) which is a complex of TATA-binding protein (TBP), which recognizes and binds to the TATA box, and (ii) 14 other protein factors which bind to TBP, and each other, but not to the DNA, and (iii) Transcription Factor IIB (TFIIB) which binds both the DNA and pol II. A promoter often contains binding sites for specific transcription factors. The effect of these transcription factors on promoter activity may determine whether the promoter activity is high or low, i.e. whether the promoter is "strong" or "weak."

In one embodiment, a constitutive or near-constitutive promoter may be used for expressing the inventive polynucleotide sequences. Examples of such promoter are the promoter of the potato ubiquitin-7 gene and the 35S promoter of cauliflower mosaic virus.

In another embodiment, the promoter is a granule bound starch synthase promoter, a potato ADP-glucose pyrophosphorylase gene promoter, or a flavonoid 3'-monooxygenase gene promoter.

In another embodiment, the promoter is a fruit-specific promoter such as the 2A11 promoter of tomato. Alternatively the tomato E8 promoter may be used.

In another embodiment, a promoter that is specific for photosynthetically-active tissues such as leaves and stems may be used. Examples of such promoters include the alfalfa E9 promoter, promoters of the rubisco small subunit gene, and rubisco activase promoters.

In another embodiment, an inducible plant gene promoter can be used. Inducible promoters regulate gene expression in response to environmental, hormonal, or chemical signals. Examples of hormone inducible promoters include auxin-inducible promoters (Baumann et al. Plant Cell 11:323-334 (1999)), cytokinin-inducible promoter (Guevara-Garcia Plant Mol. Biol. 38:743-753 (1998)), and gibberellin-responsive promoters (Shi et al. Plant Mol. Biol. 38:1053-1060 (1998)). Additionally, promoters responsive to heat, light, wounding, pathogen resistance, and chemicals such as methyl jasmonate or salicylic acid, may be used for expressing the inventive polynucleotide sequences.

Source of Elements and DNA Sequences

Any or all of the elements and DNA sequences that are described herein may be native to one or more plant genomes. Accordingly, in one particular embodiment of the present invention, all of the elements and DNA sequences, which are selected for the ultimate transfer cassette are native to the genome of the plant that is to be transformed. For instance, all of the sequences may come from a potato genome and the transgenic plant is potato. Alternatively, one or more of the elements or DNA sequences may be non-native to a plant genome that is not the same as the species of the plant to be transformed, but which function in any event in the host plant cell. Such plants include potato, tomato, and alfalfa plants. The present invention also encompasses use of one or more native regulatory elements that is one or more regulatory elements from a plant that is interfertile with the plant that is to be transformed.

In this regard, a "plant" of the present invention includes, but is not limited to, potato, tomato, alfalfa, sugarbeet, cassava, sweet potato, soybean, pea, bean, maize, wheat, rice, barley, and sorghum. "Plant" and "plant material," also encompasses plant cells, seed, plant progeny, propagule whether generated sexually or asexually, and descendents of any of these, such as cuttings or seed. "Plant material" may refer to plant cells, cell suspension cultures, callus, embryos, meristematic regions, callus tissue, leaves, roots, shoots, gametophytes, sporophytes, pollen, seeds, germinating seedlings, and microspores. Plants may be at various stages of maturity and may be grown in liquid or solid culture, or in soil or suitable media in pots, greenhouses or fields. Expression of an introduced leader, trailer or gene sequences in plants may be transient or permanent.

In this respect, a plant-derived transfer-DNA ("P-DNA") border sequence of the present invention is not identical in nucleotide sequence to any known bacterium-derived T-DNA border sequence, but it functions for essentially the same purpose. That is, the P-DNA can be used to transfer and integrate one polynucleotide into another. A P-DNA can be inserted into a tumor-inducing plasmid, such as a Ti-plasmid from *Agrobacterum* in place of a conventional T-DNA, and maintained in a bacterium strain, just like conventional transformation plasmids. The P-DNA can be manipulated so as to contain a desired polynucleotide, which is destined for integration into a plant genome via bacteria-mediated plant transformation. See Rommens et al. in WO2003/069980, US-2003-0221213, US-2004-0107455, and WO2005/004585, which are all incorporated herein by reference.

Nucleic Acid Constructs

The present invention provides constructs comprising the isolated nucleic acid molecules and polypeptide sequences of the present invention. In one embodiment, the DNA constructs of the present invention are plasmids that are capable of replication in both *E. coli* and *A. tumefaciens*, and contain a DNA segment, delineated by bacterial or plant derived borders, that can be transferred from *Agrobacterium* to plant cells.

Numerous such plasmids exist that have been described in the literature. Examples include pCAMBIA (Cambia, Australia) and pGREEN vectors (Hellens et al., Plant Mol Biol 42: 819-832, 2000). After each cloning, the cloning vector with the desired insert may be isolated and subjected to further manipulation, such as restriction digestion, insertion of new fragments or nucleotides, ligation, deletion, mutation, resection, etc. to tailor the components of the desired sequence. Once the construct has been completed, it may then be transferred to an appropriate vector for further manipulation in accordance with the manner of transformation of the host cell.

A recombinant DNA molecule of the invention typically includes a selectable marker so that transformed cells can be easily identified and selected from non-transformed cells. Examples of such markers include, but are not limited to, a neomycin phosphotransferase (nptII) gene (Potrykus et al., Mol. Gen. Genet. 199:183-188 (1985)), which confers kanamycin resistance. Cells expressing the nptII gene can be selected using an appropriate antibiotic such as kanamycin or G418. Other commonly used selectable markers include the bar gene, which confers bialaphos resistance; a mutant EPSP synthase gene (Hinchee et al., Bio/Technology 6:915-922 (1988)), which confers glyphosate resistance; and a mutant acetolactate synthase gene (ALS), which confers imidazolinone or sulphonylurea resistance (European Patent Application 154,204, 1985).

Additionally, vectors may include an origin of replication (replicons) for a particular host cell. Various prokaryotic replicons are known to those skilled in the art, and function to direct autonomous replication and maintenance of a recombinant molecule in a prokaryotic host cell.

The vectors will preferably contain selectable markers for selection in plant cells. Numerous selectable markers for use in selecting transfected plant cells include, but are not limited to, kanamycin, glyphosate resistance genes, and tetracycline or ampicillin resistance for culturing in *E. coli, A. tumefaciens* and other bacteria.

For secretion of the translated protein into the lumen of the endoplasmic reticulum, the periplasmic space or into the extracellular environment, appropriate secretion signals may be incorporated into the expressed polypeptide. The signals may be endogenous to the polypeptide, or they may be heterologous signals.

In one embodiment, a DNA construct of the current invention is designed in a manner such that a polynucleotide sequence described herein is operably linked to a tissue-specific promoter.

In a further embodiment, the DNA constructs of the current invention are designed such that the polynucleotide sequences of the current invention are operably linked to DNA or RNA that encodes interfering RNA, which corresponds to genes that code for polypeptides of interest, resulting in a decreased expression of targeted gene products.

Plant Transformation and Regeneration

The present polynucleotides and polypeptides may be introduced into a host plant cell by standard procedures known in the art for introducing recombinant sequences into a target host cell. Such procedures include, but are not limited to, transfection, infection, transformation, natural uptake, electroporation, biolistics and *Agrobacterium*. Methods for introducing foreign genes into plants are known in the art and can be used to insert a construct of the invention into a plant host, including, biological and physical plant transformation protocols. See, for example, Miki et al., 1993, "Procedure for Introducing Foreign DNA into Plants", In: Methods in Plant Molecular Biology and Biotechnology, Glick and Thompson, eds., CRC Press, Inc., Boca Raton, pages 67-88. The methods chosen vary with the host plant, and include chemical transfection methods such as calcium phosphate, microorganism-mediated gene transfer such as *Agrobacterium* (Horsch et al., Science 227:1229-31, 1985), electroporation, micro-injection, and biolistic bombardment.

Accordingly, the present invention also provides plants or plant cells, comprising the polynucleotides or polypeptides of the current invention. In one embodiment, the plants are angiosperms or gymnosperms. Beyond the ordinary meaning of plant, the term "plants" is also intended to mean the fruit, seeds, flower, strobilus tubers, etc. of the plant. The plant of the current invention may be a direct transfectant, meaning that the vector was introduced directly into the plant, such as through *Agrobacterium*, or the plant may be the progeny of a transfected plant. The progeny may be obtained by asexual or sexual reproduction of a transfected plant. The second or subsequent generation plant may or may not be produced by sexual reproduction, i.e., fertilization. Furthermore, the plant can be a gametophyte (haploid stage) or a sporophyte (diploid stage).

In this regard, the present invention contemplates transforming a plant with one or more transformation elements that genetically originate from a plant. The present invention encompasses an "all-native" approach to transformation, whereby only transformation elements that are native to plants are ultimately integrated into a desired plant via transformation. In this respect, the present invention encompasses transforming a particular plant species with only genetic transformation elements that are native to that plant species. The native approach may also mean that a particular transformation element is isolated from the same plant that is to be transformed, the same plant species, or from a plant that is sexually interfertile with the plant to be transformed.

On the other hand, the plant that is to be transformed, may be transformed with a transformation cassette that contains one or more genetic elements and sequences that originate from a plant of a different species. It may be desirable to use, for instance, a cleavage site, that is native to a potato genome in a transformation cassette or plasmid for transforming a tomato or pepper plant.

The present invention is not limited, however, to native or all-native approach. A transformation cassette or plasmid of the present invention can also comprise sequences and elements from other organisms, such as from a bacterial species. All references cited herein are explicitly incorporated by reference.

There are several different methods to measure total antioxidant capacity. See, for instance, Benzie & Strain, (1996) The Ferric Reducing Ability of Plasma (FRAP) as a Measure of "Antioxidant Power": The FRAP Assay. Anal. Biochem. 238:70-76; Rice-Evans & Miller, (1994) Total Antioxidant Status in Plasma and Body Fluids. Methods Enzymol. 234: 279-293; Wayner et al., (1985) Quantitative Measurement of the Total, Peroxyl Radical-trapping Antioxidant Capacity of Human Blood Plasma by Controlled Peroxidation. FEBS Lett. 187:33-37; Glazer, A N., (1990) Phycoerythrin Fluorescence-based Assay for Reactive Oxygen Species. Methods Enzymol 186:161-168; and Cao et al., (1993) Oxygen-radical Absorbance Capacity Assay for Antioxidants. Free Radical Biol. Med. 14:303-311. See also Held P., (Aug. 17, 2005), Performing Oxygen Radical Absorbance Capacity (ORAC) Assays with Synergy™ HT Multi-Detection Microplate Reader, ORAC Antioxidant Tests, BioTek Application Notes (biotek.com/products/techres_detail.php?id=161). See also covance.com/analytical/news_orac.php and Crowley, R., Food Product Design, Catalog Showcase, December 2004. All of these references are incorporated herein by reference.

Accordingly, assays include the ferric reducing ability of plasma (FRAP) assay and the Trolox® equivalent antioxidant capacity assay (TEAC). The TEAC assay is based on the inhibition by antioxidants of the absorbance of the cation of 2,2'-azinobis(3-ethylbenzothiazoline-6-sulfonate) (ABTS). ABTS is also a common substrate for absorbance based ELISA. The oxygen radical absorbance capacity (ORAC) assay uses fluorescein to measure antioxidant capability, and can be automated. The ORAC assay depends on the free radical damage to a fluorescent probe, such as fluorescein, that reduces its fluorescence. The degree of change is indicative of the amount of radical damage. The presence of antioxidants may therefore inhibit free radical damage to the fluorescent compound, which preserves the fluorescent signal. Reactions containing antioxidants therefore are useful for quantitating the degree the antioxidant protects against free radical damage—typically by calculating the area under the curve from the experimental sample. After subtracting the area that is obtained from a "blank" control sample, the resultant difference would be the protection conferred by the antioxidant compound. Comparison to a set of known standards allows one to calculate equivalents and compare results from different samples and experiments. Typically Trolox®, (6-hydroxy-2,5,7,8-tetrametmethylchroman-2-carboxylic acid) a water soluble vitamin E analog, is used as the calibration standard and ORAC results are expressed as Trolox® equivalents. Standardization of the ORAC assay with the use of a common calibrator in conjunction with an assay that can be performed easily on many different compounds, foods, and materials allows for an easy comparison of antioxidant capabilities of many different materials and the formation of a database. See the BioTex Application Notes (supra) for more details.

It is understood that the present invention is not limited to the particular methodology, protocols, vectors, and reagents, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include plural reference unless the context clearly dictates otherwise. Thus, for example, a reference to "a gene" is a reference to one or more genes and includes equivalents thereof known to those skilled in the art and so forth. Indeed, one skilled in the art can use the methods described herein to express any native gene (known presently or subsequently) in plant host systems.

The following examples are set forth as representative of specific and preferred embodiments of the present invention. These examples are not to be construed as limiting the scope of the invention in any manner. It should be understood that many variations and modifications can be made while remaining within the spirit and scope of the invention.

EXAMPLES

Example 1

Sequence of the Chlorogenic Acid-Inducing Cai Gene

The complementary DNAs of two MYB transcription factor genes, designated here as Cai and StMTf2, were amplified from a poly(A)+ mRNA-derived library of the white-fleshed potato variety Ranger Russet. The encoded proteins contain typical tandem R2 and R3 domains implicated in binding the major groove of DNA, and display some homology with the products of previously isolated genes such as tomato (*Solanum esculentum*) Ant1 (Genbank accession nr. ABO26064) and petunia (*Petunia hybrida*) An2 (accession AAF66727) (FIG. 1). See also SEQ ID NOs. 17-28, which relate these sequences.

SEQ ID NO.: 1 shows the sequence of the potato Cai gene. The corresponding cDNA is shown in SEQ ID NO.: 2. A modified Cai gene (mCai) was obtained by substituting two base pairs (SEQ ID NO.: 3). These mutations create an open reading frame that encodes for a protein with two amino acid substitutions. SEQ ID NO.: 4 shows the original protein, and SEQ ID NO.: 5 depicts the modified protein. The amino acids serine and proline at positions 4 and 5 are substituted by threonine and serine, respectively.

Example 2

Employment of Cai Genes as Visual Markers

Various promoters can be used to overexpress either Cai or mCai gene in plants. One such promoters is the promoter of the Ubiquitin-7 (P:Ubi7) gene (SEQ ID NO.: 8). This promoter triggers gene expression in, for instance, leaves, stems, flowers, and tubers. A binary vector containing an expression cassette for the Ubi7:mCai gene fusion, designated pSIM646, is shown in FIG. 2. Vector pSIM654 is similar to pSIM646 except that the mCai gene is replaced by Cai.

The binary vectors were introduced into *Agrobacterium tumefaciens* LBA4404 cells as follows. Competent LB4404 cells (50 μL) were incubated for 5 minutes at 37° C. in the presence of 1 μg of vector DNA, frozen for about 15 seconds in liquid nitrogen (about −196° C.), and incubated again at 37° C. for 5 minutes. After adding 1 mL of liquid broth (LB), the treated cells were grown for 3 hours at 28° C. and plated on LB/agar containing streptomycin (100 mg/L) and kanamycin (100 mg/L). The vector DNAs were then isolated from overnight cultures of individual LBA4404 colonies and examined by restriction analysis to confirm the presence of intact plasmid DNA.

Transformations of tobacco (*Nicotiana tabacum*) were carried out by growing a 10-fold dilution of overnight-grown *Agrobacterium* strains for 5-6 hours, precipitating the cells for 15 minutes at 2,800 RPM, washing them with MS liquid medium (Phytotechnology) supplemented with sucrose (3%, pH 5.7) and resuspending the cells in the same medium to an $OD_{600nm}$ of 0.2. The suspension was then used to infect leaf explants of 4-week-old in vitro grown tobacco plants. Infected tobacco explants were incubated for 2 days on co-culture medium (1/10 MS salts, 3% sucrose, pH 5.7) containing 6 g/L agar at 25° C. in a Percival growth chamber (16 hrs light) and subsequently transferred to M401 l/agar medium containing timentine (150 mg/L) and kanamycin (100 mg/L).

For potato transformations, ten-fold dilutions of overnight-grown cultures were grown for 5-6 hours, precipitated for 15 minutes at 2,800 RPM, washed with MS liquid medium (Phytotechnology) supplemented with sucrose (3%, pH 5.7), and resuspended in the same medium to 0.2 OD/600 nm. The resuspended cells were mixed and used to infect 0.4-0.6 mm internodal segments of the potato variety "Ranger Russet". Infected stems were incubated for two days on co-culture medium (1/10 MS salts, 3% sucrose, pH 5.7) containing 6 g/L agar at 22° C. in a Percival growth chamber (16 hrs light) and subsequently transferred to callus induction medium (CIM, MS medium supplemented with 3% sucrose 3, 2.5 mg/L of zeatin riboside, 0.1 mg/L of naphthalene acetic acid, and 6 g/L of agar) containing timentin (150 mg/L) and kanamycin (100 mg/L). After one month of culture on CIM, explants were transferred to shoot induction medium (SIM, MS medium supplemented with 3% sucrose, 2.5 mg/L of zeatin riboside, 0.3 mg/L of giberellic acid GA3, and 6 g/L of agar) containing timentin and kanamycin (150 and 100 mg/L respectively) until shoots arose. Shoots arising at the end of regeneration period were transferred to MS medium with 3% sucrose, 6 g/L of agar and timentin (150 mg/L). Transgenic plants were transferred to soil and placed in a growth chamber (11 hours light, 25° C.).

Many of the kanamycin resistant tobacco and potato plants accumulated anthocyanins and displayed a purple coloration. Interestingly, pSIM646 proved more effective than pSIM654 in promoting anthocyanin production. The enhanced efficacy of the mCai gene demonstrates the utility of the two point mutations described in Example 1. This improvement may be due to, for instance, reduced feed-back inhibition or modified protein phosphorylation.

A first indication for the function of mCai was obtained when, five days after explant infection, numerous individual plant cells started to accumulate purple anthocyanins (delphinidins). These pigmented cells developed into transgenic plants that produced intensely-purple leaves, stems, flowers, and roots. Transformation of plants with the pUbi7::StMTF2 gene fusion also triggered anthocyanin production although not to the same extent as shown for the first MYB transcription factor gene. Apart from pigment production, pIM646 and pSIM902 plants appeared similar to untransformed controls in terms of height, stature, leaf shape and size, and seed set (data not shown).

Although pUbi7-driven expression of both mCai and StMTF2 triggered anthocyanin biosynthesis in tobacco, this pathway was only activated by the former construct in the potato. Infection of stem explants of the potato (*Solanum tuberosum*) cultivar Bintje with the *Agrobacterium* strain carrying pSIM646 resulted in a similar production of pigments as shown for transformed tobacco. This activity was associated with a two-week delay in cell proliferation, and also resulted in a five-fold reduction of shoot regeneration frequencies if compared to control transformations. In contrast, transgenic plants derived from infections with the pSIM902 strain did not result in anthocyanin production during any phase of development (data not shown).

Nineteen purple pSIM646 potato shoots, confirmed by polymerase chain reaction (PCR)-based genotyping to contain the gene of interest, were propagated, planted in soil, and transferred to a growth chamber. After five weeks, minitubers were harvested and analyzed for weight and color. Six transgenic lines (646-2, 5, 8, 16, 19, and 20) produced relatively large minitubers with an average weight of ~42 g plant$^{-1}$ that only contained small amounts of pigment (<5% of tuber surface). Medium-sized minitubers from the eight additional lines 646-3, 4, 6, 7, 9, 10, 11, and 17 (14.9 g plant$^{-1}$) accumulated more substantial amounts of anthocyanins in the skin (10-50%), whereas the surface of the relatively small minitubers (1.3-1.6 g plant$^{-1}$) of six final lines (646-1, 12, 14, 15, 18, and 21) were intensely purple (>50%). The inverse correlation between pigment production and tuber yield could be overcome by planting transgenic potato plants in the greenhouse. Transgenic lines developed normally and, after three months, produced yields of semi-mature purple-skinned tubers (170.7±44.5 g plant$^{-1}$) that were similar to the white tuber yields obtained from transgenic controls (175.8+8.0 g plant$^{-1}$). Upon cutting the pSIM646 tubers we found, interestingly, that the tuber flesh was as white as that of control tubers. Because pUbi7 is active in most tuber tissues, the skin-specific production of delphinidins indicates that at least one anthocyanin-biosynthetic gene is not expressed in the tuber flesh. Interestingly, one-month tuber storage at 4° C. triggered some production of delphinidins in the tuber flesh, indicating that expression of the unknown gene can be induced, to some extent, by extended cold treatment.

Biochemical analyses of the most deeply colored tubers (from line 646-14) found that the total amount of phenolic compounds was not different from that of controls. However, activation of the anthocyanin pathway was associated with a strong reduction in the combined levels of the aromatic amino acids phenylalanine, tyrosine, and tryptophan (from 2.7 mg g DW$^{-1}$ in transgenic controls to 1.6 mg g DW$^{-1}$ in 646-14 tubers) (FIG. 3A). This anticipated reduction in the concentration of flavonoid substrates coincided with a reduction in the amount of the toxic skin-produced glycoalkaloids α-solanine and α-chaconine from 0.42 mg g DW$^{-1}$ to 0.22 mg g DW$^{-1}$. Furthermore, 646-14 tubers contained slightly increased levels of the quercetin derivatives rutin (from trace amounts to 0.0026 mg g$^{-1}$ DW) and quercetagin-rutinose (from trace amounts to 0.0118 mg g$^{-1}$ DW) (FIG. 3B). These changes in flux resulted in an increase in antioxidant power from 353 to 531 µM Trolox equivalents (TE) gram$^{-1}$ as determined by the oxygen radical absorbance capacity ▮▮▮▮. Together, our data demonstrate that pUbi7-driven expression of mCai triggers the biosynthesis of delphinidins in almost all plant tissues. Transgenic tubers contain intensely purple skins, reduced amounts of toxic glycoalkaloids and an increased antioxidant power.

The ability to use both the Cai gene and mCai as visual markers was not anticipated because many Myb transcription factors do not mediate the activation of the anthocyanin pathway if overexpressed, and some transcription factors only do so in specific tissues or under specific circumstances.

Visual markers are particularly important for transformations with transfer DNAs that do not contain selectable marker genes. Such selectable marker gene-free methods were recently developed (see US Patent applications US20030221213A1, US20040107455A1, and US20050034188A1, which are incorporated herein by reference). Transformed plants can be identified by applying PCR-based methods but could also be visualized if genes such as mCai are incorporated into the transfer DNA.

There are numerous promoters that can be fused to an mCai gene, or derivative thereof, to target the accumulation of anthocyanin to specific cell types. For instance, a 0.8 or 1.9-kilo basepair AtPUP1 promoter (see: Burkle et al., Plant J 34, 13-26, 2003) can be used to only overexpress an mCai gene in the epithem cells located between the xylem endings and epidermis.

Transformation of tomato with the T-DNAS of pSIM646 resulted in the development of strongly pigmented plants that produced small purple fruits.

It is also possible to employ constructs that contain a near-constitutive promoter separated from an mCai gene by a functional transposable element such as the maize Ac element. Excision of the transposable element will result in fusion of the promoter and mCai gene, resulting in the creation of purple sectors. Employment of this transposition-defined mCai gene expression system can be used to enhance the visual appearance of certain crops including tomato and pepper fruits.

Example 3

Employment of mCai Genes to Enhance the Levels of Polyphenolic Antioxidants in Potato Tubers In an attempt to direct anthocyanin production to the tuber flesh, the Ubi7 promoter of pSIM646 was replaced by the promoter of the granule-bound starch synthase (Gbss) gene (SEQ ID NO.: 6). Though not functional in tuber skin, this new promoter is active in all other tuber cell types of the tuber (Visser et al., 1991). A binary vector carrying the Ubi7:StMTF1 gene fusion, designated pSIM652, was used to produce 25 transgenic plants that were phenotypically indistinguishable from control plants. These plants were propagated and grown for three months in the greenhouse for tuber production. In contrast to the skin-specific pigment production of pSIM646 tubers, tubers of 10 pSIM652 lines specifically accumulated anthocyanins in the periderm and vascular bundles.

The harvested tubers were analyzed by high performance liquid chromatography (HPLC). See, for instance, Wen et al., "A universal HPLC method for the determination of phenolic acids in compound herbal medicines," *J Agric Food Chem.* 2005 Aug. 24; 53 (17):6624-9, Mattila & Kumpulainen, "Determination of free and total phenolic acids in plant-derived foods by HPLC with diode-array detection," *J Agric Food Chem.* 2002 Jun. 19; 50 (13):3660-7, and Shahrzad & Bitsch, "Determination of some pharmacologically active phenolic acids in juices by high-performance liquid chromatography," *J Chromatogr A.* 1996 Aug. 16; 741 (2):223-31, which are all incorporated herein by reference.

Figure 4:
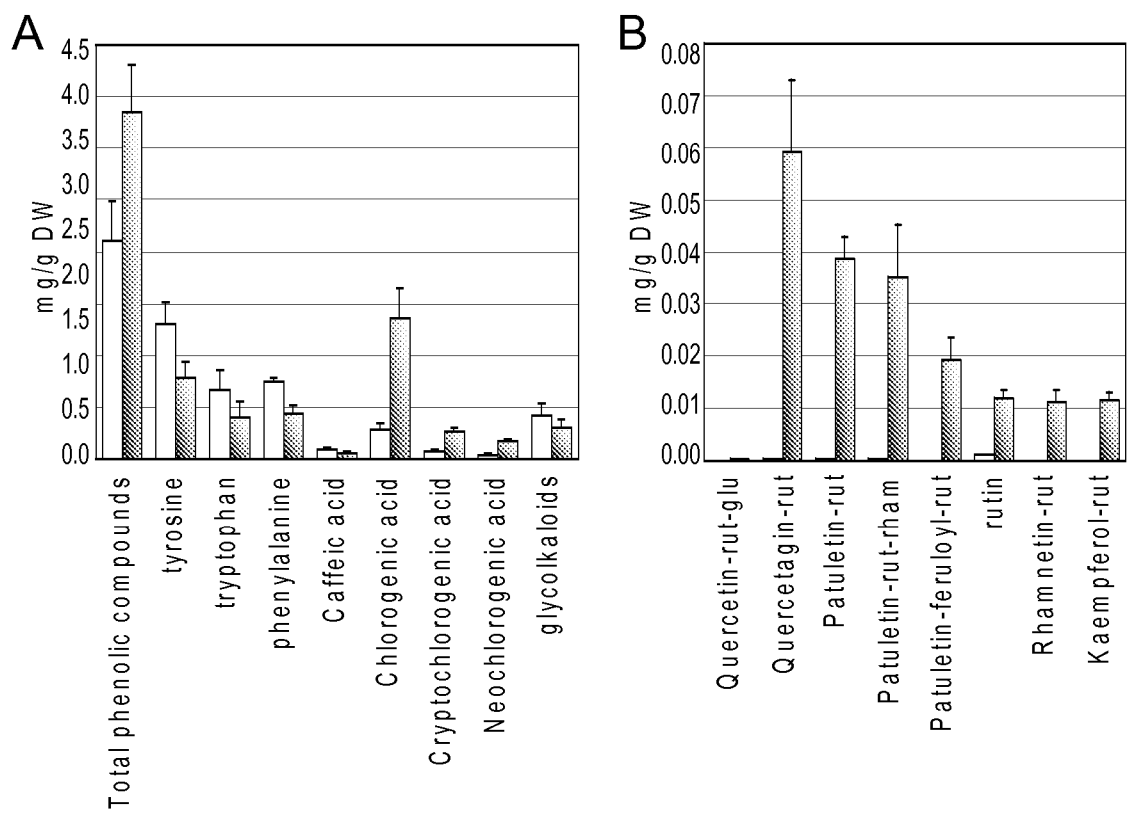
FIG. 4. HPLC analysis of Bintje tubers from a transgenic control (light bars) and line 652-30 (shaded bars). Rut=rutinose; rham=rhamnose; glu=glucoside.

Activation of the phenylpropanoid pathway in the tuber flesh resulted in an overall increase in the amount of phenolic compounds from 2.2 mg g DW$^{-1}$ for controls to 3.3 mg g DW$^{-1}$ for 652-30 tubers (FIG. 4A). This increased flux was associated with a similar reduction in the amount of the aromatic amino acids as determined above for pSIM646-14 tubers (FIG. 4A) and, importantly, triggered an unexpected four-fold increase in the levels of the phenolic compound chlorogenic acid and its derivatives (0.43 mg g$^{-1}$ DW) if compared to controls (1.83 mg g$^{-1}$ DW) (FIG. 4A). This biochemical change resulted in formation of a typical grayish tint on cut tubers of pSIM646 lines if exposed for several hours to air. The enhancement in chlorogenic acid levels was much greater than the 1.5-fold increase accomplished by overexpressing the hydroxycinnamoyl-CoA quinate: hydroxycinnamoyl transferase gene (Niggeweg et al., 2004). Furthermore, transgenic tubers accumulated about 20-fold higher flavonol levels than the purple-skinned pSIM646 tubers (0.176 mg g$^{-1}$ DW) (FIG. 4B). In addition to the quercetin derivatives that were also produced in 646-14 tubers, we found 652-30 tubers to contain the derivatives patuletin-rutinose, patuletin-rutinose-rhamnose, patuletin-feruloyl-rutinose, and rhamnetin-rutinose. The 652-30 tubers also contained small amounts of kaempferol-rutinose (0.012 mg g$^{-1}$ DW (FIG. 4B). The altered pathway flux was associated with an overall increase in antioxidant power from 310 μM TE gram$^{-1}$ for control tubers to 645 μM TE gram$^{-1}$. Thus, overexpression of the StMTF1 gene in the tuber flesh activates not only the anthocyanin biosynthetic pathway but also at least one other branch of the phenylpropanoid pathway.

Another compound that is strongly increased in concentration is caffeoyl putrescine, from about 0.02 mg/g DW to about 0.18 mg/g DW. We also found an about two-fold reduction in spermine and spermidine levels, from about 0.15 mg/g DW to about 0.07 mg/g DW.

As an alternative to the Gbss promoter, it is also possible to use the promoter of the potato ADP-glucose pyrophosphorylase gene (Agp) (SEQ ID NO.: 7). This promoter generally secures higher gene expression levels than the Gbss promoter. Other tuber-specific promoters can also be used, and include the patatin promoter and the flavonoid 3'-monooxygenase (Fmo) gene promote.

It is also possible to employ inducible promoters. Strong pathogen-inducible promoters can be used to increase the chlorogenic acid levels in infected tissues. Because chlorogenic acid plays a role in plant defense responses, the pathogen-inducible expression of the mCai gene enhances plant tolerance against certain diseases. An example of a pathogen-inducible promoter is the Asparagus Pr1 promoter (AoPR1).

Example 4 mCai Gene Overexpression and Silencing of the F35H Gene

To further boost kaempferol biosynthesis, two new expression cassettes were developed for the present invention, aimed at specifically silencing the anthocyanin biosynthetic genes encoding dihydroflavonol reductase (Dfr) and flavonoid-3',5'-hydroxylase (F35h) (Jung et al., 2005), respectively. Vector pSIM1079 contains two copies of an 187-bp Dfr gene fragment (SEQ ID NO.: 12) inserted as inverted repeat between the Ubi7 promoter and the convergently-oriented 35S promoter of cauliflower mosaic virus (CaMV) (FIG. 2). Through collisional transcription, this new type of silencing construct produces non-processed and variably-sized RNAs that activate gene silencing at least as effectively as the products of unidirectional gene silencing constructs (Yan et al., 2007). The silencing cassette was flanked by an expression cassette for the hygromycin phosphotransferase (hptII) selectable marker gene. The inverted repeat of the second vector pSIM1080 contains 267-bp fragments of the F35h gene (SEQ ID NO.: 9) but is otherwise identical to pSIM1079. A BamHI-SpeI construct comprising two copies of this fragment, separated by a spacer and positioned as inverted repeat is shown in SEQ ID NO.: 10. If inserted between either a promoter and terminator or two convergently-oriented promoters, the resulting silencing construct can be used to reduce F35H gene expression levels. A binary vector containing one such silencing constructs between T-DNA borders, designated pSIM656. An alternative silencing strategy exploits a fragment of the promoter of the F35H gene. An inverted repeat comprising two F35H promoter fragments is shown in SEQ ID NO.: 11. This sequence can be inserted between either a promoter and terminator or two convergent 'driver' promoters to silence the F35H gene. One example of a binary vector carrying a promoter-based silencing construct to target expression of the F35H gene is shown in FIG. 2 as pSIM1166. Silencing of the F35H gene may restore yield losses that are associated with the constitutive overexpression of the mCai gene.

Infection of explants from the purple pSIM652-30 plants with an *Agrobacterium* strain carrying pSIM1079 resulted in the formation of 77 kanamycin and hygromycin resistant shoots. Most of these shoots (56) were phenotypically indistinguishable from control shoots, whereas only 21 shoots displayed a weak reduction in pigment formation. This finding indicates that Dfr gene silencing is not sufficient to eliminate anthocyanin biosynthesis in potato. In contrast, 37 of 100 shoots obtained from a transformation with pSIM1080 lost their ability to produce any anthocyanins. The green pSIM1080 shoots were confirmed by the polymerase chain reaction (PCR) to contain the F35h gene silencing construct. Thus, F35h rather than Dfr plays a key role in anthocyanin production in potato varieties such as Bintje. The ability to prevent coloration through F35h gene silencing can be used as an assay to identify silenced plants without an immediate need to perform transcript analyses.

Figure 5:
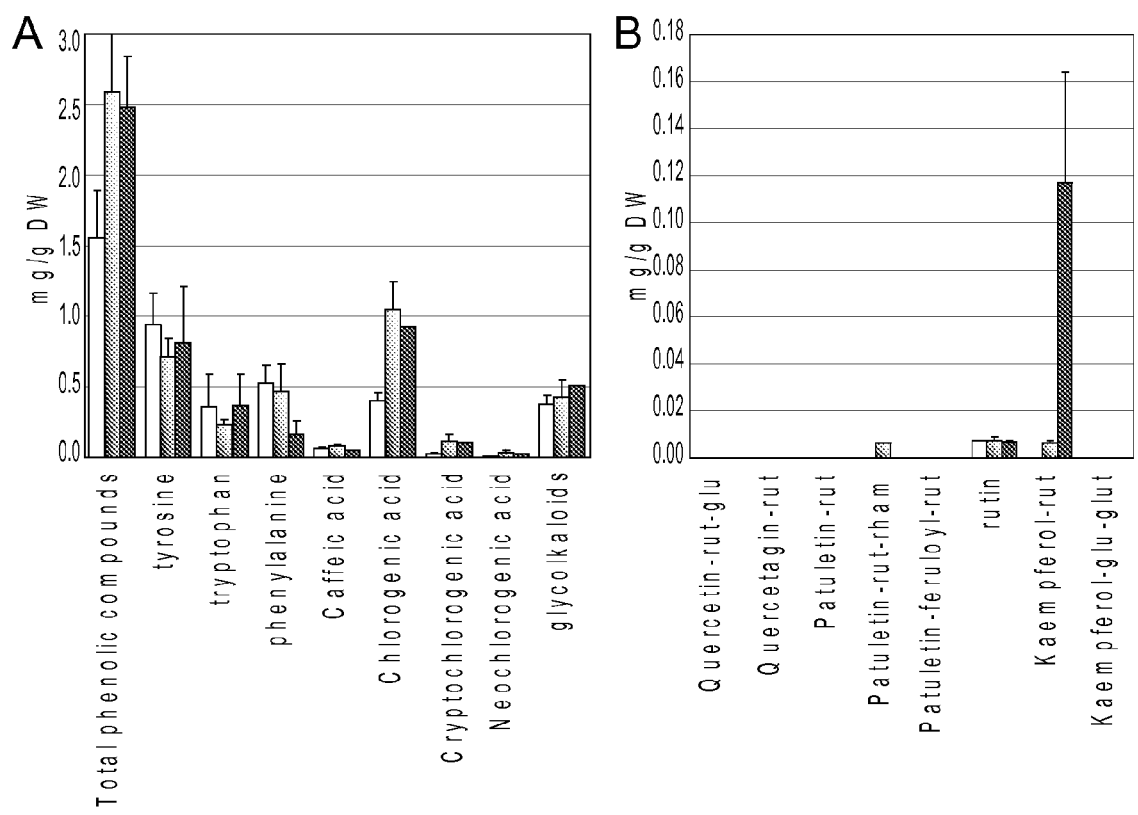
FIG. 5. HPLC analysis of Bintje tubers from a transgenic control (light bars), line 652-30 (shaded bars), and doubly-transformed line 652-30/1080-4 (dark bars).

Twenty-five PCR-positive shoots for each construct were planted in soil and transferred to the greenhouse. The absence of purple pigments in leaves, stems, and flowers of pSIM1080 plants continued to distinguish these plants from both controls and pSIM1079 plants. Based on tuber phenotypes, double transformants were divided into three different groups. Plant 1080-15 produced tubers that were phenotypically indistinguishable from the original transformant 652-30. Most likely, this plant contained F35h gene silencing constructs that were, due to position integration effects, not expressed in tubers. A second group of plants (1080-5, 6, 20 and 26) produced tubers that lacked any anthocyanins. The tubers of these plants resembled control tubers both phenotypically and biochemically. These results indicate that full F35h gene silencing results in feed-back inhibition of the phenylpropanoid pathway. The most interesting tubers were obtained from a third group of plants (1080-4, 10, 24, 28, and 30). The tubers of this group displayed intermediary phenotypes whereby anthocyanin production was diminished but not eliminated. These tubers contained similarly-low levels of phenylalanine as the original transformant (FIG. 5A). They also accumulated high levels of both chlorogenic acid and its derivatives cryptochlorogenic acid and neochlorogenic acid (FIG. 5A). Even more importantly, the tubers also contained about 100-fold higher levels of kaempferol as control tubers (FIG. 5B).

Given that potato is the most-consumed vegetable or fruit (171 g day$^{-1}$), replacement of current low-kaempferol varieties by the Pokedot varieties would result in a dramatic increase in the average daily intake of kaempferol and chlorogenic acid.

For commercial purposes, it is desirable to employ a plant-derived transfer DNA that contains both an expression cassette for the mCai gene and a silencing construct for the F35H gene. Any of the above-described promoters can be used to drive expression, either near-constitutively or time- or tissue-specifically, of (i) the mCai gene, and (ii) either at least one fragment of the F35H gene or its promoter.

Instead of mCai, it is possible to use other genes that activate anthocyanin biosynthesis such as tomato Ant1, *Arabidopsis* Pap1, and the maize Lc/C1 system.

It is also possible to transform potato varieties that produce high levels of delphinidins with a construct designed to silence the F35H gene. Examples of such potato varieties include "All Blue" and "Purple Valley". Transformation with any high-anthocyanin variety with a silencing construct that contains a promoter that is active in leaf and stem tissues will result in the regeneration of shoots that are not purple but green (or less-purple). These green shoots can be allowed to root and planted into soil. If the promoter of the silencing construct is also expressed in tubers, the resulting tubers will be less purple than the tubers of the original untransformed varieties, and can even be free of any visual purple coloration. A biochemical analysis of these tubers shows that, while containing greatly reduced levels of anthocyanins, they still produce similar levels of phenolic compounds, such as flavonols, as the untransformed plant.

Figure 6:
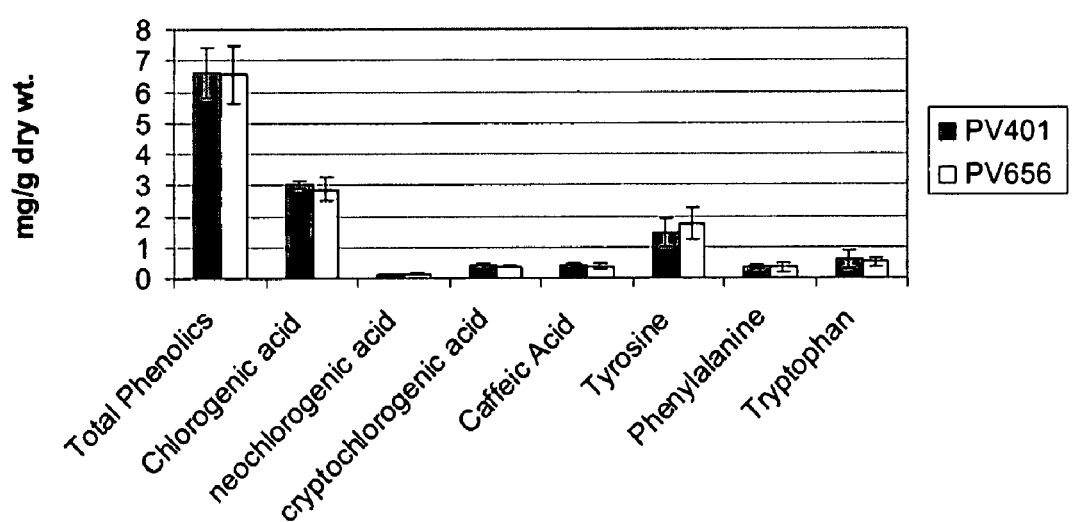
FIG. 6. HPLC analysis of (i) the purple tubers from a transgenic Purple Valley control PV401 (dark bars) and (ii) the white tubers from a transgenic Purple Valley 656 line (white bars).

One example relates to the variety Purple Valley. Upon transformation with pSIM656, plants were obtained that produced tubers containing reduced levels of anthocyanins, especially delphinidins. Biochemical analysis of the anthocyanin-free tubers of line PV656-1 demonstrated similar levels of total phenolics including chlorogenic acid as the levels in tubers of Purple Valley plants transformed with a control construct (FIG. 6). This experiment represents the first example for downregulated expression of the F35 gene in transgenic plants.

Example 5 mCai Gene Overexpression Coupled with Silencing of the Dfr Gene

A fragment of the dihydroflavonol reductase (Dfr) gene is used to produce a silencing construct that, if expressed in plants, mediates the down-regulated expression of the Dfr gene. An example of a DNA fragment isolated from this gene is shown in SEQ ID NO.: 12. A silencing construct comprising two copies of the fragment, inserted as inverted repeat between a tuber-expressed promoter and a terminator, was positioned between T-DNA borders. The resulting transfer DNA also contained an expression cassette for the nptII gene. Introduction of the transfer DNA into a plant lowered anthocyanin production in transgenic potato plants but not to the same extent as observed for silencing constructs that target F35H gene expression. Reduced expression of the Dfr gene in combination with overexpressed mCai, will increase the concentration of flavonols and chlorogenic acid in transformed plant cells and plants.

Example 6

Chalcone Accumulation

The binary vector pSIM1252 carrying a silencing construct for the Chi gene was used to retransform pSIM646 tobacco plants. The silencing construct contains two fragments of the Chi gene (SEQ ID NO.: 15), inserted as inverted repeat between a strong promoter and terminator.

A 10-fold dilution of an overnight-grown *Agrobacterium* culture was grown for five to six hours, precipitated for 15 minutes at 2,800 RPM, washed with MS liquid medium (PhytoTechnology, KS) supplemented with sucrose (3%, pH 5.7) and resuspended in the same medium to 0.2 OD/600 nm. The suspension was then used to infect leaf explants of 4-week old in vitro grown *Nicotiana tabacum* plants. Infected tobacco explants were incubated for two days on co-culture medium (1/10 MS salts, 3% sucrose, pH 5.7) containing 6 g/L agar at 25° C. in a Percival growth chamber (16/8 hr photoperiod) and subsequently transferred to M401/agar (PhytoTechnology) medium containing timentin (150 mg/L) and kanamycin (100 mg/L).

Transgenic plants were found to contain much lower levels of anthocyanins and, instead, accumulated yellow chalcones. Some of these chalcones leaked, through the roots, into the root environment where they can provide protection against certain diseases and pests such as nematodes.

In a similar way, the Chi gene can be silenced in the purple tubers of either existing varieties such as Purple Valley or varieties that were modified to overexpress the Cai gene. Any fragment of the potato Chi gene (shown in SEQ ID NO.: 16), preferably greater than ~100-bp, can be used to develop a silencing construct.

Example 7 mCai Gene Overexpression Coupled with Silencing of the F3h Gene

It is possible to silence the F3h gene in a similar way as described above for the F35h and Dfr genes. This application is particularly useful in plants producing cyanindins, and will lead to a reduction in the accumulation of this type of anthocyanin while increasing the levels of kaempferol.

Example 8

Application of the Technologies to Other Crops

Constructs containing the mCai gene operably linked to P:Ubi7 were introduced into tomato in a similar manner as described for potato. Hypocotyls were used as efficient explant material. The resulting near-constitutive overexpression of mCai triggered a strong accumulation of anthocyanin pigments. Preferred promoters to drive mCai are either specific for tomato fruits or upregulated in tomato fruits. Examples of such promoters include the 2A11 promoter shown in SEQ ID NO.: 13, and the E8 promoter shown in SEQ ID NO.: 14. Transgenic tomato plants containing the mCai gene driven by a fruit-specific promoter will contain increased amounts of phenolic compounds such as flavonols and/or chlorogenic acid in their fruits. Other crops that can be transformed with the mCai gene to increase the amount of certain phenolic compounds include pepper, eggplant, and tobacco.

Example 9

Enhanced Tolerance Against a Phytopathogen

Chlorogeneic acid is known to display antimicrobial activity. For instance, the slightly increased levels of chlorogenic acid in transgenic plants overexpressing the Hqt gene displayed some enhanced tolerance against a strain of the bacterial pathogen *Pseudomonas syringae*.

Transgenic potato plants overexpressing the mCai gene will display enhanced tolerance against a bacterial pathogen such as *Erwinia carotovora*, causal agent of tuber soft rot, and *Streptomyces scabies*, which causes common scab.

Transgenic tomato plants that overexpress mCai will display enhanced tolerance against bacterial pathogens including *Xanthomonas vesicatoria*, which causal bacterial spot, and the bacterial speck-causing *Pseudomonas syringae*.

Bacterial diseases will also be controlled in mCai-expressing sweet pepper, hot pepper, and eggplant.

Similarly, mCai gene overexpression can trigger partial tolerance against fungal pathogens such as *Cercospora nicotianae* and *Fusarium oxysporum*.

Example 10

Accelerated Suberization

Native periderm, the dermal tissue covering the potato tuber, provides an essential barrier to pathogens and dehydration. The cell walls of the outer group of peridermal cells, phellem cells, are laminated with suberin, a complex, inert biopolyester, which provides a protective barrier for the tuber. Suberin is composed of two distinctly different biochemical components: a polyphenolic component and a polyaliphatic component. Wounding breaches the native periderm, but induces new depositions of these suberin components as part of wound-periderm development during wound-healing. Rapid suberization of wounded areas is essential to avoid infection. Increased levels of phenolic compounds in transgenic plants overexpressing the mCai gene will accelerate the suberization process.

Example 11

Enhanced Visual Appeal

The mCai gene can be used to enhance the visual appeal of plants. In one application, this gene is employed to produce plants that develop red or purple spots or sectors on their leaves, flowers, tubers, or roots. This application inserts a transposable element between a strong promoter and the mCai gene in a similar way as described before for the insertion of a transposable element between a promoter and the gus gene (Rommens et al., Plant Sci 74: 99-106). In our case, the insertion will prevent gene expression and anthocyanin production. However, occasional excision will generally restore mCai gene function. Based on the frequency and timing of excision, plants will develop specific color patterns. These patterns may be used as visual "markers" to indicate that a particular variety is genetically modified.

Another example links the mCai gene to a tissue-specific promoter. Fusion to the bean Pal2 promoter (Liang et al., Proc Natl Acad Sci USA 86: 9284-9288) can lead to a vascular-specific accumulation of anthocyanins in tobacco. Any tissue-specific promoter could be linked to the Cai gene to create specific patterns. Furthermore, promoters can be used to develop "indicator" plants that express the Cai gene conditionally. Such indicator plants can be used to monitor factors that activate the promoter driving the Cai gene such as "low nitrogen" or "high carbon dioxide."

What is claimed is:

1. A method for increasing the level of an antioxidant in a plant, comprising transforming a plant to overexpress (i) a chlorogenic acid-inducing gene (Cai) that comprises the amino acid sequence of SEQ ID NO. 4 or SEQ ID NO. 5, or (ii) a polynucleotide encoding a Cai protein that shares at least 90% sequence identity with SEQ ID NO. 4 or SEQ ID NO. 5, in a plant or plant product, wherein the level of the antioxidant, chlorogenic acid, is increased in the transformed plant or its product compared to the level of chlorogenic acid in a non-transformed plant or product thereof.

2. The method of claim 1, further comprising co-transforming the plant with a construct that expresses a polynucleotide that brings about downregulation or inhibition of at least one of (i) the F35h gene, (ii) the F3h gene, (iii) the Dfr gene, and (iv) the Chi gene, and which thereby increases the level of antioxidant in the plant or a product made from the plant.

3. The method of claim 1, further comprising co-transforming the plant with a construct that expresses a polynucleotide that brings about downregulation or inhibition of endogenous Chi gene expression in the transformed plant or its product, wherein the plant or product that is co-transformed with the Chi gene has increased levels of the antioxidant, chalcone, after the Chi gene is downregulated or inhibited.

4. The method of claim 1, further comprising co-transforming the plant with a construct that expresses a polynucleotide that modifies the expression of any endogenous flavonoid pathway gene in the transformed plant or its product, wherein the transformed plant or its product has increased antioxidant levels.

5. The method of claim 1, wherein the Cai gene expresses a protein that shares at least 90% sequence identity to the sequence of SEQ ID NO: 5.

6. The method of claim 1, wherein the plant is a solanaceous crop plant.

7. The method of claim 6, wherein the solanaceous crop plant is a potato plant, a tobacco plant, a tomato plant, a *capsicum* plant, or an eggplant.

8. The method of claim 1, wherein the Cai gene expresses a protein that shares at least 90% sequence identity to the sequence of SEQ ID NO: 5.

9. A transformed plant, comprising in its genome (A) a Cai gene or a polynucleotide that encodes a protein that shares at least 90% sequence identity with the protein encoded by the Cai gene, and (B) a nucleic acid that downregulates or inhibits the endogenous expression of at least one of (i) the F35h gene, (ii) the F3h gene, (iii) the Dfr gene, and (iv) the Chi gene.

10. The transformed plant of claim 9, wherein the plant is a solanaceous crop plant.

11. The transformed plant of claim 10, wherein the solanaceous crop plant is a potato plant, a tobacco plant, a tomato plant, a *capsicum* plant, or an eggplant.

12. A plant product obtained from the transformed plant of claim 10 wherein the product has increased levels of at least two of chlorogenic acid, kaempferol, and chalcone compared to a product that is not obtained from the transformed plant.

13. The plant product of claim 12, wherein the product is a potato and wherein the potato has increased levels of at least two of chlorogenic acid, kaempferol, and chalcone compared to a potato that is not obtained from the transformed plant.

14. The plant product of claim 12, wherein the product is a tomato and wherein the tomato has increased levels of at least two of chlorogenic acid, kaempferol, and chalcone compared to a tomato that is not obtained from the transformed plant.

15. The plant product of claim 12, wherein the product is a *capsicum* product that has increased levels of at least two of chlorogenic acid, kaempferol, and chalcone compared to a *capsicum* product that is not obtained from the transformed plant.

16. The plant product of claim 12, wherein the product has at least a 3-fold increase in chlorogenic acid levels compared to chlorogenic acid levels from an equivalent product that is obtained from a non-transformed plant of the same species.

17. The plant product of claim 12, wherein the product has at least a 10-fold increase in kaempferol levels compared to kaempferol levels from an equivalent product that is obtained from a non-transformed plant of the same species.

18. The transformed plant of claim 9, wherein the Cai gene expresses a protein that shares at least 90% sequence identity to the sequence of SEQ ID NO: 5.

19. A method for altering the level of an antioxidant in a potato plant that produces a tuber with blue, red, or purple pigments, comprising expressing in a blue- or purple-skinned potato plant a nucleic acid that downregulates or inhibits the endogenous expression of at least one of (i) the F35h gene, (ii) the F3h gene, and (iii) the Chi gene, wherein the level of antioxidants in the plant expressing the nucleic acid is different to a blue- or purple-skinned potato plant of the same variety that does not express the nucleic acid.

20. The method of claim 19, wherein the potato plant is selected from the group consisting of AC Blue Pride, AC Domino, Adirondack Blue, All Blue, Bleue d'Auvergne, Blue Mac, Brigus, British Columbia Blue, Caribe, Congo, Cowhorn, Glacier Blue, La Crotte d'Ours, Mayan Gold, Michigan Purple, OAC Royal Gold, Purple Peruvian, Purple Viking, Ruby Pulsiver's Blue Noser, True Blue, and Vitelette.

21. The method of claim 19, wherein a tuber obtained from the plant that expresses the nucleic acid has increased levels of at least one of kaempferol and chalcone antioxidants.

22. A blue, red, or purple pigmented potato that comprises in its genome a nucleic acid that downregulates or inhibits the endogenous expression of at least one of (i) the F35h gene, (ii) the F3h gene, and (iii) the Chi gene.

23. The method of claim 1, wherein the expression of the Cai gene or the polynucleotide in the skin cells of a tuber causes the level of glycoalkaloid in the skin of the tuber to be lower than the level of glycoalkaloid in the skin of a tuber that does not overexpress the Cai gene or polynucleotide.

24. A tuber, comprising a nucleic acid construct that expresses the chlorogenic acid inducing gene (Cai) gene in at least one tissue of the tuber.

25. The method of claim 23, wherein the Cai gene expresses a protein that shares at least 90% sequence identity to the sequence of SEQ ID NO: 5.

26. An isolated polynucleotide encoding (i) a Cai protein comprising the sequence of SEQ ID NO. 4 or SEQ ID NO. 5, or (ii) a variant that is at least 90% identical in amino acid sequence to SEQ ID NO. 4 or SEQ ID NO 5, wherein overexpressing the variant in a plant results in an increased level of chlorogenic acid compared to the level of chlorogenic acid in a non-transformed plant.

27. A method for increasing the level of an antioxidant in a plant, comprising expressing the isolated polynucleotide of claim 26 in cells of a plant transformed with the polynucleotide, wherein expression of the isolated polynucleotide is associated with an increase in the antioxidant levels in the plant compared to a plant not transformed with the polynucleotide.

28. A plant product obtained from the transformed plant of claim 10, wherein the plant product comprises (A) a Cai gene or a polynucleotide that encodes a protein that shares at least 90% sequence identity with the protein encoded by the Cai gene, and (B) a nucleic acid that downregulates or inhibits the endogenous expression of at least one of (i) the F35h gene, (ii) the F3h gene, (iii) the Dfr gene, and (iv) the Chi gene.

* * * * *